United States Patent
Frey et al.

(10) Patent No.: US 11,011,708 B2
(45) Date of Patent: *May 18, 2021

(54) ELECTRON TRANSPORT LAYER STACK FOR AN ORGANIC LIGHT-EMITTING DIODE

(71) Applicants: Novaled GmbH, Dresden (DE); Samsung SDI Co. Ltd., Gyeonggi-do (KR)

(72) Inventors: Julien Frey, Sarrebourg (FR); Domagoj Pavicic, Dresden (DE); Carsten Rothe, Dresden (DE); Volodymyr Senkovskyy, Dresden (DE); Francois Cardinali, Dresden (DE); Hyungsun Kim, Suwon-si (KR); Byungku Kim, Suwon-si (KR)

(73) Assignees: Novaled GmbH, Dresden (DE); Samsung SDI Co. Ltd., Gyeonggi-do (KR)

( * ) Notice: Subject to any disclaimer, the term of this patent is extended or adjusted under 35 U.S.C. 154(b) by 321 days.

This patent is subject to a terminal disclaimer.

(21) Appl. No.: 15/788,431

(22) Filed: Oct. 19, 2017

(65) Prior Publication Data

US 2018/0114920 A1 Apr. 26, 2018

(30) Foreign Application Priority Data

Oct. 24, 2016 (EP) .................................... 16195344

(51) Int. Cl.
| | | |
|---|---|---|
| *H01L 51/56* | (2006.01) | |
| *H01L 51/50* | (2006.01) | |
| *H01L 51/00* | (2006.01) | |
| *C07D 495/04* | (2006.01) | |
| *C07D 401/10* | (2006.01) | |
| *C07D 251/24* | (2006.01) | |
| *C07D 221/18* | (2006.01) | |

(52) U.S. Cl.
CPC ........ *H01L 51/0067* (2013.01); *C07D 221/18* (2013.01); *C07D 251/24* (2013.01); *C07D 401/10* (2013.01); *C07D 495/04* (2013.01); *H01L 51/0052* (2013.01); *H01L 51/0054* (2013.01); *H01L 51/0071* (2013.01); *H01L 51/0072* (2013.01); *H01L 51/508* (2013.01); *H01L 51/0077* (2013.01); *H01L 51/5012* (2013.01); *H01L 51/5016* (2013.01); *H01L 51/5076* (2013.01); *H01L 51/56* (2013.01)

(58) Field of Classification Search
CPC ............... H01L 51/0067; H01L 51/508; H01L 51/0072; H01L 51/0071; H01L 51/0054; H01L 51/0052; H01L 51/56; H01L 51/5076; H01L 51/5016; H01L 51/0077; H01L 51/0062; H01L 51/5072; H01L 51/0032; H01L 51/005; H01L 51/0064; H01L 51/0095; H01L 51/5048; H01L 51/50; H01L 51/5012; H01L 2251/53; H01L 2251/5384; C07D 495/04; C07D 401/10; C07D 251/24; C07D 221/18; C07D 239/70; C07D 221/02; C09K 11/00; C09K 11/06

See application file for complete search history.

(56) References Cited

U.S. PATENT DOCUMENTS

| | | | |
|---|---|---|---|
| 8,431,046 | B2 | 4/2013 | Zeika et al. |
| 9,118,019 | B2 | 8/2015 | Limmert et al. |
| 9,502,660 | B2 | 11/2016 | Dorok et al. |
| 2003/0165711 | A1 | 9/2003 | Kim et al. |
| 2015/0034915 | A1* | 2/2015 | Kim ..................... H01L 51/0072 257/40 |
| 2015/0325800 | A1* | 11/2015 | Ito .......................... H05B 33/20 257/40 |
| 2017/0309830 | A1* | 10/2017 | Kim ..................... C07D 239/74 |

FOREIGN PATENT DOCUMENTS

| | | | | | |
|---|---|---|---|---|---|
| EP | 2826781 | A1 * | 1/2015 | | |
| EP | 3182478 | A1 * | 6/2017 | ........... | H01L 51/005 |
| JP | 2001-291593 | A | 10/2001 | | |
| JP | 2008-195623 | A | 8/2008 | | |
| WO | WO-03007658 | A8 * | 2/2004 | ............. | C07C 13/62 |
| WO | 2007/107356 | A1 | 9/2007 | | |
| WO | 2011/154131 | A1 | 12/2011 | | |
| WO | 2013/079217 | A1 | 6/2013 | | |
| WO | 2013/079676 | A1 | 6/2013 | | |
| WO | 2013/079678 | A1 | 6/2013 | | |
| WO | WO-2014141725 | A1 * | 9/2014 | ........... | C07D 307/77 |

* cited by examiner

Primary Examiner — Lucas A Stelling
Assistant Examiner — Rachel Simbana
(74) Attorney, Agent, or Firm — Eversheds Sutherland (US) LLP

(57) ABSTRACT

The present invention relates to an organic light-emitting diode (OLED) including an ETL stack of at least two electron transport layers, wherein the first electron transport layer comprises a charge transporting compound and the second electron transport layer comprises an acridine compound and an alkali metal salt and/or alkali metal organic complex, a method of manufacturing the same and a device comprising the OLED.

14 Claims, 2 Drawing Sheets

ELECTRON TRANSPORT LAYER STACK FOR AN ORGANIC LIGHT-EMITTING DIODE

CROSS REFERENCE TO RELATED APPLICATION

This application claims priority to European Application No. 16195344.3, filed Oct. 24, 2016. The contents of this application is hereby incorporated by reference.

TECHNICAL FIELD

The present invention relates to an organic light-emitting diode (OLED) including an ETL stack of at least two electron transport layers, wherein the first electron transport layer comprises a charge transporting compound and the second electron transport layer comprises an acridine compound and an alkali metal salt and/or alkali metal organic complex, a method of manufacturing the same and a device comprising the OLED.

BACKGROUND ART

Organic light-emitting diodes (OLEDs), which are self-emitting devices, have a wide viewing angle, excellent contrast, quick response, high brightness, excellent driving voltage characteristics, and color reproduction. A typical OLED includes an anode, a hole transport layer HTL, an emission layer EML, an electron transport layer ETL, and a cathode, which are sequentially stacked on a substrate. In this regard, the HTL, the EML, and the ETL are thin films formed from organic compounds.

US 2006/057427 A1 refers to an organic electroluminescent element that includes a pair of electrodes and a plurality of organic compound layers being disposed between the pair of electrodes. The organic compound layers include a luminescent layer containing a blue phosphorescent luminescent material and a host material having the lowest excited triplet energy (T1) of 272 kJ/mol (65 kcal/mol) or more, and hole transport layers. One of the hole transport layers is a layer adjacent to the luminescent layer, and when the ionization potentials of the luminescent layer, the hole transport layer adjacent to the luminescent layer, and another of the hole transport layers, respectively, designated to Ip1, Ip2 and Ip3, the relationship Ip1>Ip2>Ip3 is satisfied.

US 2015/034915 A1 refers to an organic light-emitting device includes a first electrode, a second electrode, and an organic layer interposed between the first electrode and the second electrode, wherein the organic layer includes an emission layer.

US 2004/209116 A1 refers to an organic light emitting devices (OLEDs), and more specifically to efficient OLEDs having an emissive layer having host material with a wide energy gap.

When a voltage is applied to the anode and the cathode, holes injected from the anode move to the EML, via the HTL, and electrons injected from the cathode move to the EML, via the ETL. The holes and electrons recombine in the EML to generate excitons. When the excitons drop from an excited state to a ground state, light is emitted. The injection and flow of holes and electrons should be balanced, so that an OLED having the above-described structure has excellent efficiency and/or a long lifetime.

WO2011154131A1 relates to an electronic device comprising at least one organic semiconducting material according to the following formula (A): wherein R1-4 are independently selected from H, halogen, CN, substituted or unsubstituted C1-C20-alkyl or heteroalkyl, C6-C20-aryl or C5-C20-heteroaryl, C1-C20-alkoxy or C6-C20-aryloxy, Ar is selected from substituted or unsubstituted C6-C20-aryl or C5-C20-heteroaryl, and R5 is selected from substituted or unsubstituted C6-C20-aryl or C5-C20-heteroaryl, H, F or formula (B).

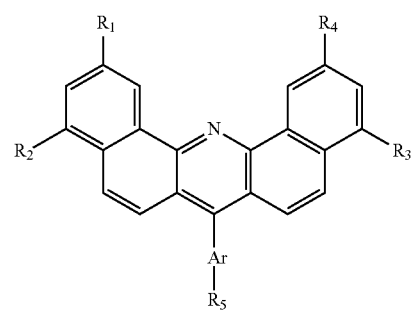

(A)

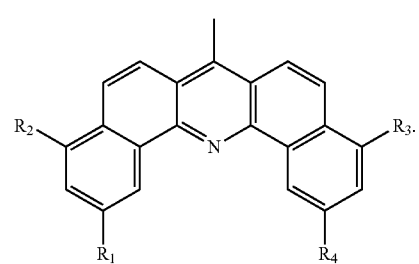

(B)

PCT-KR2015-012551 relates to a compound for an organic optoelectric device represented by Chemical Formula I, an organic optoelectric device, and a display device are provided.

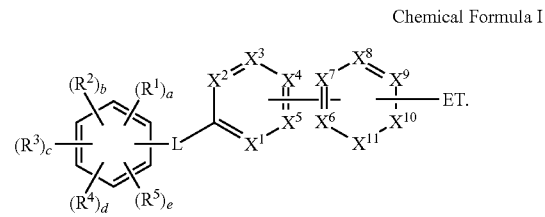

Chemical Formula I

In light of the prior art, there remains a need to improve performance of OLEDs and organic semiconductor materials, in particular achieve higher efficiency and/or longer lifetime through improving the characteristics of the compounds comprised therein.

DISCLOSURE

Aspects of the present invention provide an organic light-emitting diode (OLED) comprising an emission layer and at least two electron transport layers (ETLs) for increasing the efficiency, such as the external quantum efficiency EQE, low operating voltage and long lifetime, for top and/or bottom emission organic light-emitting diodes (OLED).

Another aspect of the present invention provides a method of manufacturing the OLED.

Another aspect of the present invention provides an electronic device comprising at least one OLED.

According to an aspect of the present invention, there is provided an electroluminescent device comprising an anode, a cathode, an emission layer arranged between the cathode and the anode, a first electron transport layer and a second electrode transport layer, wherein the first electron transport layer and the second electron transport layer are arranged between the emission layer and the cathode, the first electron transport layer is arranged closer to the emission layer than the second electron transport layer and the second electron transport layer is arranged closer to the cathode than the first electron transport layer; wherein a) the first electron transport layer comprises a first matrix compound of formula (I):

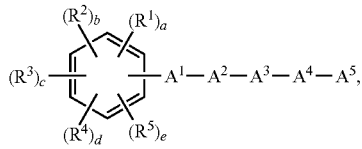

wherein
$A^1$, $A^2$, $A^3$ and $A^4$ is independently selected from single bond, an unsubstituted or substituted $C_6$ to $C_{30}$ arylene and an unsubstituted or substituted $C_1$ to $C_{30}$ heteroarylene;

$A^5$ is selected from an unsubstituted or substituted $C_6$ to $C_{40}$ aryl group and/or from an unsubstituted or substituted $C_2$ to $C_{40}$ heteroaryl group, $R^1$ to $R^5$ are independently a substituted or unsubstituted $C_6$ to $C_{30}$ aryl group, a substituted or unsubstituted $C_2$ to $C_{30}$ heteroaryl group;

wherein in the substituted group, at least one hydrogen is replaced by (i) deuterium,
(ii) a halogen,
(iii) a $C_2$ to $C_{60}$ tertiary amino group, wherein the nitrogen atom of the tertiary amino group is substituted with two independently selected $C_1$ to $C_{30}$ hydrocarbyl groups or the nitrogen atom of the $C_2$ to $C_{60}$ tertiary amino group forms a $C_1$ to $C_{30}$ heterocyclic group,
(iv) a $C_1$ to $C_{22}$ silyl group,
(v) a $C_1$ to $C_{30}$ alkyl group,
(vi) a $C_1$ to $C_{10}$ alkylsilyl group,
(vii) a $C_6$ to $C_{22}$ arylsilyl group,
(viii) a $C_3$ to $C_{30}$ cycloalkyl group,
(ix) a $C_2$ to $C_{30}$ heterocycloalkyl group,
(x) a $C_6$ to $C_{30}$ aryl group,
(xi) a $C_2$ to $C_{30}$ heteroaryl group,
(xii) a $C_1$ to $C_{20}$ alkoxy group,
(xiii) a $C_1$ to $C_{30}$ perfluoro-hydrocarbyl group,
(xiv) a $C_1$ to $C_{10}$ trifluoroalkyl group, or
(xv) a cyano group;

a to e are independently an integer of 0 or 1 and $4 \leq a+b+c+d+e \leq 5$; and b) the second electron transport layer comprises an alkali metal salt or an alkali metal organic complex and a second matrix compound according to formula (II):

A-W$_f$ (II), wherein

A is an acridine derivative of an unsubstituted or substituted benzoacridine or an unsubstituted or substituted dibenzoacridine;

W is independently selected from a substituted or unsubstituted $C_{16}$ to $C_{48}$ aryl group comprising 2 to 8 aromatic rings, and/or a substituted or unsubstituted $C_{10}$ to $C_{33}$ heteroaryl group comprising at least 2 to 8 aromatic rings; wherein the substituents are selected from deuterium, $C_1$ to $C_{12}$ alkyl and $C_1$ to $C_{12}$ alkoxy;

f is 1 or 2, preferably f is 1.

The alkali metal salt or alkali metal organic complex contained in the electron transport layers may not emit light under the operation condition of an electroluminescent device, for example an OLED.

The first and second matrix compounds are organic compounds and are free of a metal. The matrix compounds contained in the electron transport layers may not emit light under the operation condition of an electroluminescent device, for example an OLED.

Operation condition of an electroluminescent device, for example an OLED are described in the experimental part of this specification.

According to a further aspect of the invention the electroluminescent device can be an organic light emitting diode OLED.

The compound represented by formula I and II, and a composition comprising the compound represented by formula I or II have strong electron transport characteristics to increase charge mobility and stability and thereby to improve luminance efficiency, voltage characteristics, and life-span characteristics.

In the present specification "$A^1$, $A^2$, $A^3$ and $A^4$ is independently selected from single bond" means that if "$A^1$, $A^2$, $A^3$ and $A^4$" are selected to be a single bond, "$A^1$, $A^2$, $A^3$ and $A^4$" forms together one single bond.

In the present specification "$A^1$, $A^2$, $A^3$ and $A^4$ is independently selected from single bond" means that if at least two directly connected members thereof, for example "$A^1$, $A^2$", are selected to be a single bond, these connected members forms together one single bond.

In the present specification "$A^1$, $A^2$, $A^3$ and $A^4$ is independently selected from single bond" means that if at least three directly connected members thereof, for example "$A^2$, $A^3$, $A^4$", are selected to be a single bond, these directly connected members forms together one single bond.

In the present specification the term "wherein in the substituted group, at least one hydrogen is replaced by" relates to $A^1$, $A^2$, $A^3$, $A^3$ and $A^5$; to $R^1$ to $R^5$; to $Ar^1$; to L; and to ET; if not otherwise stated.

In the present specification, when a definition is not otherwise provided, "substituted" refers to one substituted with a deuterium, $C_1$ to $C_{12}$ alkyl and $C_1$ to $C_{12}$ alkoxy.

In the present specification, when a definition is not otherwise provided, an "alkyl group" may refer to an aliphatic hydrocarbon group. The alkyl group may refer to "a saturated alkyl group" without any double bond or triple bond.

The alkyl group may be a $C_1$ to $C_{12}$ alkyl group. More specifically, the alkyl group may be a $C_1$ to $C_{10}$ alkyl group or a $C_1$ to $C_6$ alkyl group. For example, a $C_1$ to $C_4$ alkyl group includes 1 to 4 carbons in alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

The term "cycloalkyl" refers to saturated hydrocarbyl groups derived from a cycloalkane by formal abstraction of one hydrogen atom from a ring atom comprised in the corresponding cycloalkane. Examples of the cycloalkyl group may be a cyclopropyl group, a cyclobutyl group, a cyclopentyl group, a cyclohexyl group, a methylcyclohexyl group, an adamantly group and the like.

Under heterocycloalkyl, it is understood a group derived by formal abstraction of one ring hydrogen from a saturated heterocyclic ring in a compound comprising at least one such ring.

The term "hetero" is understood the way that at least one carbon atom, in a structure which may be formed by covalently bound carbon atoms, is replaced by another polyvalent atom. Preferably, the heteroatoms are selected from B, Si, N, P, O, S; more preferably from N, P, O, S.

In the present specification "aryl group" may refers to a group including at least one hydrocarbon aromatic moiety, and all the elements of the hydrocarbon aromatic moiety may have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like.

The aryl group may include a monocyclic, polycyclic or fused ring polycyclic (i.e., rings sharing adjacent pairs of carbon atoms) functional group.

The term "heteroaryl" as used herewith refers to aryl groups in which at least one carbon atom is substituted by a heteroatom, preferably selected from N, O, S, B or Si. Heteroarylene refers to groups to which two further moieties are attached.

The subscribed number n in $C_n$-heteroaryl merely refers to the number of carbon atoms excluding the number of heteroatoms. In this context, it is clear that a $C_5$ heteroarylene group is an aromatic compound comprising five carbon atoms, such as pyridyl.

In the present specification, the single bond may refer to a direct bond.

In the context of the present invention, "different" means that the compounds do not have an identical chemical structure.

The term "free of", "does not contain", "does not comprise" does not exclude impurities which may be present in the compounds prior to deposition. Impurities have no technical effect with respect to the object achieved by the present invention.

The term "contacting sandwiched" refers to an arrangement of three layers whereby the layer in the middle is in direct contact with the two adjacent layers.

In the specification, hole characteristics refer to an ability to donate an electron to form a hole when an electric field is applied and that a hole formed in the anode may be easily injected into the emission layer and transported in the emission layer due to conductive characteristics according to a highest occupied molecular orbital (HOMO) level.

In addition, electron characteristics refer to an ability to accept an electron when an electric field is applied and that electron formed in the cathode may be easily injected into the emission layer and transported in the emission layer due to conductive characteristics according to a lowest unoccupied molecular orbital (LUMO) level.

According to another embodiment a method of manufacturing the same is provided.

Advantageous Effects

Surprisingly, it was found that an ETL layer stack of the invention solves the problem underlying the present invention by being superior over the organic electroluminescent devices known in the art, in particular with respect cd/A efficiency. High cd/A efficiency is important for high efficiency and thereby increased battery life of a mobile device, for example a mobile display device.

The inventors have surprisingly found that particular good performance can be achieved when using the organic electroluminescent device as a fluorescent blue device.

The specific arrangements mentioned herein as preferred were found to be particularly advantageous.

Likewise, some compounds falling within the scope of the broadest definition of the present invention have surprisingly be found to be particularly well performing with respect to the mentioned properties of cd/A efficiency. These compounds are discussed herein to be particularly preferred.

Further an organic electroluminescent device having high efficiency and/or long life-span may be realized.

Hereinafter, an ETL layer stack comprising a first and second electron transport layer according to an embodiment are described.

First Electron Matrix Compound

According to a further embodiment, the first electron transport layer may comprise or consist of a first matrix compound of formula (I):

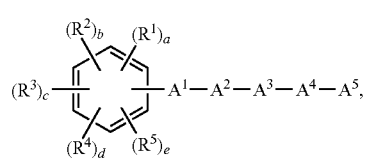

wherein $A^1$, $A^2$, $A^3$ and $A^4$ is independently selected from single bond, an unsubstituted or substituted $C_6$ to $C_{30}$ arylene and an unsubstituted or substituted $C_1$ to $C_{30}$ heteroarylene;

$A^5$ is selected from an unsubstituted or substituted $C_6$ to $C_{40}$ aryl group and/or from an unsubstituted or substituted $C_2$ to $C_{40}$ heteroaryl group;

$R^1$ to $R^5$ are independently a substituted or unsubstituted $C_6$ to $C_{30}$ aryl group, a substituted or unsubstituted $C_2$ to $C_{30}$ heteroaryl group;

wherein in the substituted group, at least one hydrogen is replaced by (i) deuterium, (ii) a halogen, (iii) a $C_2$ to $C_{60}$ tertiary amino group, wherein the nitrogen atom of the tertiary amino group is substituted with two independently selected $C_1$ to $C_{30}$ hydrocarbyl groups or the nitrogen atom of the $C_2$ to $C_{60}$ tertiary amino group forms a $C_1$ to $C_{30}$ heterocyclic group, (iv) a $C_1$ to $C_{22}$ silyl group, (v) a $C_1$ to $C_{30}$ alkyl group, (vi) a $C_1$ to $C_{10}$ alkylsilyl group, (vii) a $C_6$ to $C_{22}$ arylsilyl group, (viii) a $C_3$ to $C_{30}$ cycloalkyl group, (ix) a $C_2$ to $C_{30}$ heterocycloalkyl group, (x) a $C_6$ to $C_{30}$ aryl group, (xi) a $C_2$ to $C_{30}$ heteroaryl group, (xii) a $C_1$ to $C_{20}$ alkoxy group, (xiii) a $C_1$ to $C_{30}$ perfluoro-hydrocarbyl group, (xiv) a $C_1$ to $C_{10}$ trifluoroalkyl group, or
(xv) a cyano group; and
a to e are independently an integer of 0 or 1 and $4 \leq a+b+c+d+e \leq 5$.

According to a further embodiment, the first electron transport layer comprises a first electron matrix compound according to formula (Ia):

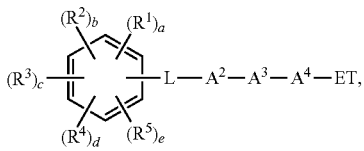

wherein, in formula Ia,
$A^2$ is selected from $C_6$ to $C_{12}$ aryl and $C_1$ to $C_{11}$ heteroaryl;
$A^3$ and $A^4$ are a single bond; and
$R^1$ to $R^5$ are independently a substituted or unsubstituted $C_6$ to $C_{30}$ aryl group, a substituted or unsubstituted $C_2$ to $C_{30}$ heteroaryl group;
a to e are independently an integer of 0 or 1 and $4 \leq a+b+c+d+e \leq 5$;
L is a single bond, a substituted or unsubstituted $C_6$ to $C_{30}$ arylene group, or a substituted or unsubstituted $C_2$ to $C_{30}$ heteroarylene group;
ET is a unsubstituted $C_6$ to $C_{40}$ aryl or a unsubstituted $C_5$ to $C_{40}$ heteroaryl group or a substituted $C_6$ to $C_{40}$ aryl or a substituted $C_5$ to $C_{40}$ heteroaryl group;
wherein in the substituted group, at least one hydrogen is replaced by
(i) deuterium,
(ii) a halogen,
(iii) a $C_2$ to $C_{60}$ tertiary amino group, wherein the nitrogen atom of the $C_2$ to $C_{60}$ tertiary amino group is substituted with two independently selected $C_1$ to $C_{30}$ hydrocarbyl groups or forms a $C_1$ to $C_{30}$ heterocyclic group,
(iv) a $C_1$ to $C_{22}$ silyl group,
(v) a $C_1$ to $C_{30}$ alkyl group,
(vi) a $C_1$ to $C_{10}$ alkylsilyl group,
(vii) a $C_6$ to $C_{22}$ arylsilyl group,
(viii) a $C_3$ to $C_{30}$ cycloalkyl group,
(ix) a $C_2$ to $C_{30}$ heterocycloalkyl group,
(x) a $C_6$ to $C_{30}$ aryl group,
(xi) a $C_2$ to $C_{30}$ heteroaryl group,
(xii) a $C_1$ to $C_{20}$ alkoxy group,
(xiii) a $C_1$ to $C_{30}$ perfluoro-hydrocarbyl group,
(xiv) a $C_1$ to $C_{10}$ trifluoroalkyl group, or
(xv) a cyano group.

Formula (Ia) falls under the definition of Formula I, wherein $A^1$ is L and $A^2$ is selected from $C_6$ to $C_{12}$ aryl and $C_1$ to $C_{11}$ heteroaryl; $A^3$ and $A^4$ are a single bond and $A^5$=ET.

According to a further embodiment, in formula (Ia):
$R^1$ to $R^5$ are independently a substituted or unsubstituted $C_6$ to $C_{12}$ aryl group, a substituted or unsubstituted $C_5$ to $C_9$ heteroaryl group;
a to e are independently an integer of 0 or 1 and $4 \leq a+b+c+d+e \leq 5$;
L is a single bond, a substituted or unsubstituted $C_6$ to $C_{12}$ arylene group, or a substituted or unsubstituted $C_5$ to $C_9$ heteroarylene group;
ET is a unsubstituted $C_6$ to $C_{18}$ aryl or a unsubstituted $C_5$ to $C_{20}$ heteroaryl group or a substituted $C_6$ to $C_{18}$ aryl or a substituted $C_5$ to $C_{20}$ heteroaryl group; and
wherein in the substituted group, at least one hydrogen is replaced by
(xvi) deuterium,
(xvii) a $C_1$ to $C_{12}$ alkyl group,
(xviii) a $C_6$ to $C_{12}$ aryl group,
(xix) a $C_5$ to $C_9$ heteroaryl group,
(xx) a $C_1$ to $C_{12}$ alkoxy group.

According to a further embodiment, $Ar^1$ is phenyl or biphenyl and L is a single bond.

According to a further embodiment, a first electron transport layer comprises a first electron matrix compound according to formula (Ib)

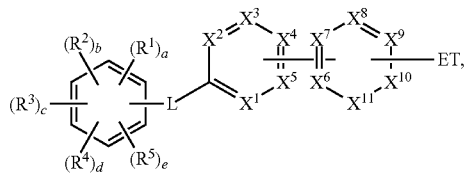

wherein in formula Ib:
$X^1$ to $X^{11}$ are independently, N, C, or $CR^a$;
$R^a$ is independently, hydrogen, deuterium, a $C_1$ to $C_{30}$ alkyl group, a $C_3$ to $C_{30}$ cycloalkyl group, a $C_6$ to $C_{30}$ aryl group, a $C_6$ to $C_{30}$ diarylamine group, a $C_1$ to $C_{30}$ alkoxy group, a $C_3$ to $C_{21}$ silyl group, a $C_3$ to $C_{21}$ silyloxy group, a $C_1$ to $C_{30}$ alkylthiol group, a $C_6$ to $C_{30}$ arylthiol group, a halogen, a $C_1$ to $C_{30}$ halogenated hydrocarbyl group, a cyano group;
$R^1$ to $R^5$ are independently a substituted or unsubstituted $C_6$ to $C_{30}$ aryl group, a substituted or unsubstituted $C_2$ to $C_{30}$ heteroaryl group;
a to e are independently an integer of 0 or 1 and $4 \leq a+b+c+d+e \leq 5$,
L is a single bond, a substituted or unsubstituted $C_6$ to $C_{30}$ arylene group, a substituted or unsubstituted $C_2$ to $C_{30}$ heteroarylene group, and
ET is a unsubstituted $C_6$ to $C_{40}$ aryl or a unsubstituted $C_2$ to $C_{40}$ heteroaryl group, or a substituted $C_6$ to $C_{40}$ aryl or a substituted $C_2$ to $C_{40}$ heteroaryl group; and
wherein in the substituted group, at least one hydrogen is replaced by
(i) deuterium,
(ii) a halogen,
(iii) a $C_1$ to $C_{60}$ tertiary amino group, wherein the nitrogen atom of the $C_2$ to $C_{60}$ tertiary amino group is substituted with two independently selected $C_1$ to $C_{30}$ hydrocarbyl groups or forms a $C_1$ to $C_{30}$ heterocyclic group,
(iv) a $C_1$ to $C_{22}$ silyl group,
(v) a $C_1$ to $C_{30}$ alkyl group,
(vi) a $C_1$ to $C_{10}$ alkylsilyl group,
(vii) a $C_6$ to $C_{22}$ arylsilyl group,
(viii) a $C_3$ to $C_{30}$ cycloalkyl group,
(ix) a $C_2$ to $C_{30}$ heterocycloalkyl group,
(x) a $C_6$ to $C_{30}$ aryl group,
(xi) a $C_2$ to $C_{30}$ heteroaryl group,
(xii) a $C_1$ to $C_{20}$ alkoxy group,
(xiii) a $C_1$ to $C_{30}$ perfluoro-hydrocarbyl group,
(xiv) a $C_1$ to $C_{10}$ trifluoroalkyl group, or
(xv) a cyano group.

Preferably, $R^a$ is independently selected from hydrogen, deuterium, a $C_1$ to $C_{30}$ alkyl group, a $C_3$ to $C_{30}$ cycloalkyl group, a $C_6$ to $C_{30}$ aryl group, or a $C_1$ to $C_{30}$ alkoxy group.

According to a further embodiment, a first electron transport layer comprises a first electron matrix compound according to formula (Ic)

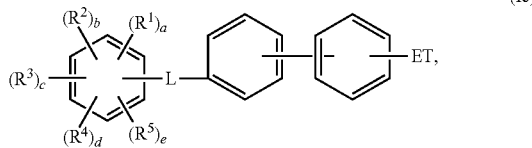

wherein in formula Ic:
$R^1$ to $R^5$ are independently a substituted or unsubstituted $C_6$ to $C_{30}$ aryl group, a substituted or unsubstituted $C_2$ to $C_{30}$ heteroaryl group;
a to e are independently an integer of 0 or 1 and $4 \leq a+b+c+d+e \leq 5$,
L is a single bond, a substituted or unsubstituted $C_6$ to $C_{30}$ arylene group, a substituted or unsubstituted $C_2$ to $C_{30}$ heteroarylene group, and
ET is a unsubstituted $C_6$ to $C_{40}$ aryl or a unsubstituted $C_2$ to $C_{40}$ heteroaryl group, or a substituted $C_6$ to $C_{40}$ aryl or a substituted $C_2$ to $C_{40}$ heteroaryl group;
wherein in the substituted group, at least one hydrogen is replaced by
(i) deuterium,
(ii) a halogen,
(iii) a $C_1$ to $C_{60}$ tertiary amino group, wherein the nitrogen atom of the $C_2$ to $C_{60}$ tertiary amino group is substituted with two independently selected $C_1$ to $C_{30}$ hydrocarbyl groups or forms a $C_1$ to $C_{30}$ heterocyclic group,
(iv) a $C_1$ to $C_{22}$ silyl group,
(v) a $C_1$ to $C_{30}$ alkyl group,
(vi) a $C_1$ to $C_{10}$ alkylsilyl group,
(vii) a $C_6$ to $C_{22}$ arylsilyl group,
(viii) a $C_3$ to $C_{30}$ cycloalkyl group,
(ix) a $C_2$ to $C_{30}$ heterocycloalkyl group,
(x) a $C_6$ to $C_{30}$ aryl group,
(xi) a $C_2$ to $C_{30}$ heteroaryl group,
(xii) a $C_1$ to $C_{20}$ alkoxy group,
(xiii) a $C_1$ to $C_{30}$ perfluoro-hydrocarbyl group,
(xiv) a $C_1$ to $C_{10}$ trifluoroalkyl group, or
(xv) a cyano group.

According to a further embodiment, a first electron transport layer comprises a first electron matrix compound according to formula (Ic)

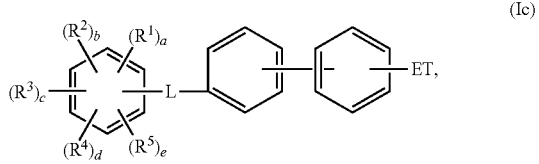

wherein in formula Ic:
$R^1$ to $R^5$ are independently a substituted or unsubstituted $C_6$ to $C_{30}$ aryl group, a substituted or unsubstituted $C_2$ to $C_{30}$ heteroaryl group;
a to d are 1;
e is 0; and
L is a single bond, a substituted or unsubstituted $C_6$ to $C_{30}$ arylene group, a substituted or unsubstituted $C_2$ to $C_{30}$ heteroarylene group, and
ET is a unsubstituted $C_6$ to $C_{40}$ aryl or a unsubstituted $C_2$ to $C_{40}$ heteroaryl group, or a substituted $C_6$ to $C_{40}$ aryl or a substituted $C_2$ to $C_{40}$ heteroaryl group;
wherein in the substituted group, at least one hydrogen is replaced by
(i) deuterium,
(ii) a halogen,
(iii) a $C_1$ to $C_{60}$ tertiary amino group, wherein the nitrogen atom of the $C_2$ to $C_{60}$ tertiary amino group is substituted with two independently selected $C_1$ to $C_{30}$ hydrocarbyl groups or forms a $C_1$ to $C_{30}$ heterocyclic group,
(iv) a $C_1$ to $C_{22}$ silyl group,
(v) a $C_1$ to $C_{30}$ alkyl group,
(vi) a $C_1$ to $C_{10}$ alkylsilyl group,
(vii) a $C_6$ to $C_{22}$ arylsilyl group,
(viii) a $C_3$ to $C_{30}$ cycloalkyl group,
(ix) a $C_2$ to $C_{30}$ heterocycloalkyl group,
(x) a $C_6$ to $C_{30}$ aryl group,
(xi) a $C_2$ to $C_{30}$ heteroaryl group,
(xii) a $C_1$ to $C_{20}$ alkoxy group,
(xiii) a $C_1$ to $C_{30}$ perfluoro-hydrocarbyl group,
(xiv) a $C_1$ to $C_{10}$ trifluoroalkyl group, or
(xv) a cyano group.

According to a further embodiment, in the substituted group one hydrogen atom is replaced by
(i) deuterium,
(ii) a halogen,
(iii) a $C_1$ to $C_{60}$ tertiary amino group, wherein the nitrogen atom of the $C_2$ to $C_{60}$ tertiary amino group is substituted with two independently selected $C_1$ to $C_{30}$ hydrocarbyl groups or forms a $C_1$ to $C_{30}$ heterocyclic group,
(iv) a $C_1$ to $C_{22}$ silyl group,
(v) a $C_1$ to $C_{30}$ alkyl group,
(vi) a $C_1$ to $C_{10}$ alkylsilyl group,
(vii) a $C_6$ to $C_{22}$ arylsilyl group,
(viii) a $C_3$ to $C_{30}$ cycloalkyl group,
(ix) a $C_2$ to $C_{30}$ heterocycloalkyl group,
(x) a $C_6$ to $C_{30}$ aryl group,
(xi) a $C_2$ to $C_{30}$ heteroaryl group,
(xii) a $C_1$ to $C_{20}$ alkoxy group,
(xiii) a $C_1$ to $C_{30}$ perfluoro-hydrocarbyl group,
(xiv) a $C_1$ to $C_{10}$ trifluoroalkyl group, or
(xv) a cyano group.

Preferably, $R^1$ to $R^5$ are independently selected from are independently a substituted or unsubstituted $C_6$ to $C_{18}$ aryl group or $C_5$ to $C_{18}$ heteroaryl group, more preferred from a substituted or unsubstituted $C_6$ to $C_{18}$ aryl group. Preferably, $R^1$ to $R^5$ are unsubstituted.

Particularly good performance can be achieved when the compound of formula I is selected in this range, in particular in layers which are deposited in vacuum.

One or more substituents may be selected from $C_4$ to $C_{12}$ alkyl or $C_4$ to $C_{12}$ alkoxy. Particularly good properties in solution processed layers may be obtained, when the compound of formula I is selected in this range.

Preferably, L is selected from a single bond or unsubstituted phenyl.

According to a further embodiment, the ET group is a $C_2$ to $C_{30}$ heteroaryl group, preferably ET is selected from formula E1 or E2:

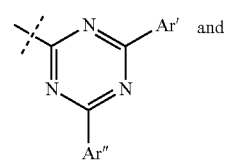

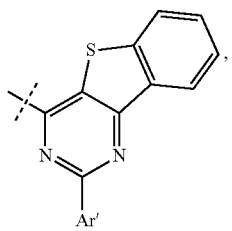

E2 wherein
Ar' and Ar'' are independently selected from $C_6$ to $C_{18}$ aryl, preferably from $C_6$ to $C_{12}$ aryl.

Preferably, ET is selected from formula E1. Preferably, the compound of formula I is essentially non-emissive.

In the context of the present specification the term "essentially non-emissive" means that the contribution of the compound or layer to the visible emission spectrum from the device is less than 10%, preferably less than 5% relative to the visible emission spectrum. The visible emission spectrum is an emission spectrum with a wavelength of about ≥380 nm to about ≤780 nm.

According to a further aspect of the invention, the reduction potential of the first electron transport matrix compound, if measured under the same conditions by cyclic voltammetry against $Fc/Fc^+$ in tetrahydrofuran, may have a value which is less negative than the value obtained for triphenylphosphine oxide and more negative than the value obtained for tetrakis(quinoxalin-5-yloxy)zirconium.

Under these conditions the reduction potential of triphenylphosphine oxide is about −3.06 V and the reduction potential of tetrakis(quinoxalin-5-yloxy)zirconium is about −1.78 V.

According to a further aspect of the invention, the reduction potential of the first electron transport matrix compound, if measured under the same conditions by cyclic voltammetry against $Fc/Fc^+$ in tetrahydrofuran, may has a value which is less negative than the respective value obtained for triphenylphosphine oxide, preferably less negative than the respective value for bis(4-(9H-carbazol-9-yl)phenyl)-(phenyl)phosphine oxide, more preferably less negative than the respective value for 3-([1,1'-biphenyl]-4-yl)-5-(4-(tert-butyl)phenyl)-4-phenyl-4H-1,2,4-triazole, even more preferably less negative than the respective value for pyrene, most preferably less negative than the respective value for 2,7-di-pyrenyl-9,9-spirobifluorene, also preferably less negative than the respective value for 4,7-diphenyl-1,10-phenanthroline, also preferably less negative than the respective value for 2,4,7,9-tetraphenyl-1,10-phenanthroline, also preferably less negative than the respective value for 7-([1,1'-biphenyl]-4-yl)dibenzo[c,h]acridine, also preferably less negative than the respective value for 2,4,6-triphenyltriazine, and still preferably less negative than the respective value for 2,4,6-tri(biphenyl-4-yl)-1,3,5-triazine.

According to a further aspect of the invention, the reduction potential of the first electron transport matrix compound, if measured under the same conditions by cyclic voltammetry against $Fc/Fc^+$ in tetrahydrofuran, may has the value which is more negative than the respective value obtained for tetrakis(quinoxalin-5-yloxy)zirconium, preferably more negative than the respective value for 4,4'-bis(4,6-diphenyl-1,3,5-triazin-2-yl)-1,1'-biphenyl, most preferably more negative than the respective value for 2,4,6-tri(biphenyl-4-yl)-1,3,5-triazine.

According to a further aspect of the invention, the reduction potential of the first electron matrix compound may be selected less negative than −2.35 V and more negative than −2.14 V, preferably less negative than −2.3 V and more negative than −2.16 V, more preferably less negative than −2.25 V and more negative than −2.16 V, when measured against $Fc/Fc^+$ in tetrahydrofuran.

The reduction potential can be determined by cyclic voltammetry with potenioststic device Metrohm PGSTAT30 and software Metrohm Autolab GPES at room temperature. The reduction potentials given at particular compounds were measured in an argon de-aerated, dry 0.1M THF solution of the tested substance, under argon atmosphere, with 0.1M tetrabutylammonium hexafluorophosphate supporting electrolyte, between platinum working electrodes and with an Ag/AgCl pseudo-standard electrode (Metrohm Silver rod electrode), consisting of a silver wire covered by silver chloride and immersed directly in the measured solution, with the scan rate 100 mV/s. The first run was done in the broadest range of the potential set on the working electrodes, and the range was then adjusted within subsequent runs appropriately. The final three runs were done with the addition of ferrocene (in 0.1M concentration) as the standard. The average of potentials corresponding to cathodic and anodic peak of the studied compound, after subtraction of the average of cathodic and anodic potentials observed for the standard $Fc^+/Fc$ redox couple, afforded finally the values reported above. All studied compounds as well as the reported comparative compounds showed well-defined reversible electrochemical behaviour.

Preferably, the dipole moment of the compound of formula I may be selected ≥0 and ≤2.3 Debye, preferably ≥0.3 and ≤2 Debye, also preferred ≥0.4 and ≤2 Debye, also preferred ≥0.4 and ≤0.8 Debye. Particularly good performance is obtained when the compound of formula I is selected in this range.

The dipole moment $|\vec{\mu}|$ of a molecule containing N atoms is given by:

$$\vec{\mu} = \sum_i^N q_i \vec{r}_i$$

$$|\vec{\mu}| = \sqrt{\mu_x^2 + \mu_y^2 + \mu_z^2}$$

where $q_i$ and $\vec{r}_i$ are the partial charge and position of atom i in the molecule.

The dipole moment is determined by a semi-empirical molecular orbital method.

The values in Table 2 and 3 were calculated using the method as described below.

The partial charges and atomic positions may be obtained using either the DFT functional of Becke and Perdew BP with a def-SV(P) basis or the hybrid functional B3LYP with a def2-TZVP basis set as implemented in the program package TURBOMOLE V6.5. If more than one conformation is viable, the conformation with the lowest total energy is selected to determine the dipole moment.

According to another aspect, the compound of formula I may have a glass transition temperature (Tg) selected between ≤125° C. and ≤200° C., preferably ≤130 ° C. and ≤180° C.

The glass transition temperature can be measured under nitrogen and using a heating rate of 10 K per min in a Mettler Toledo DSC 822e differential scanning calorimeter as described in DIN EN ISO 11357, published in March 2010.
Particularly preferred may be compounds of formula I with the following structures A1 to A11:
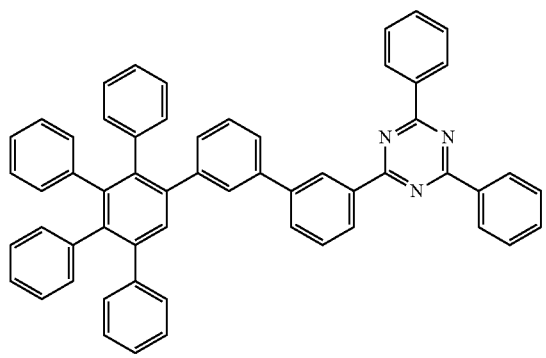
A1
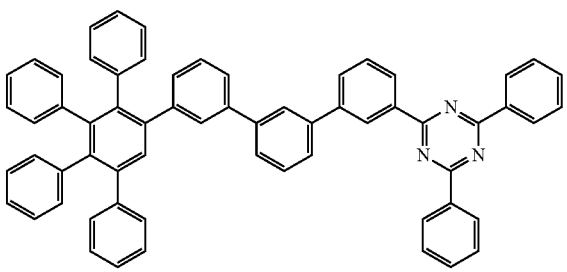
A2
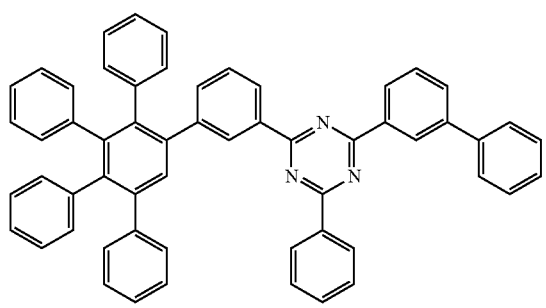
A3
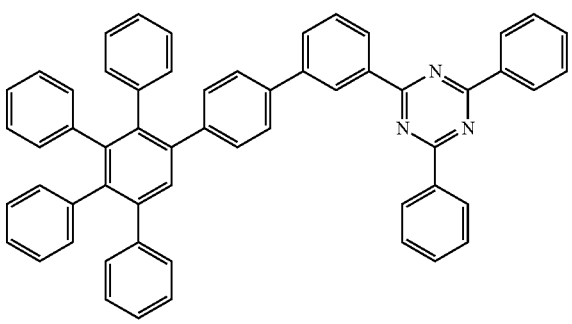
A4
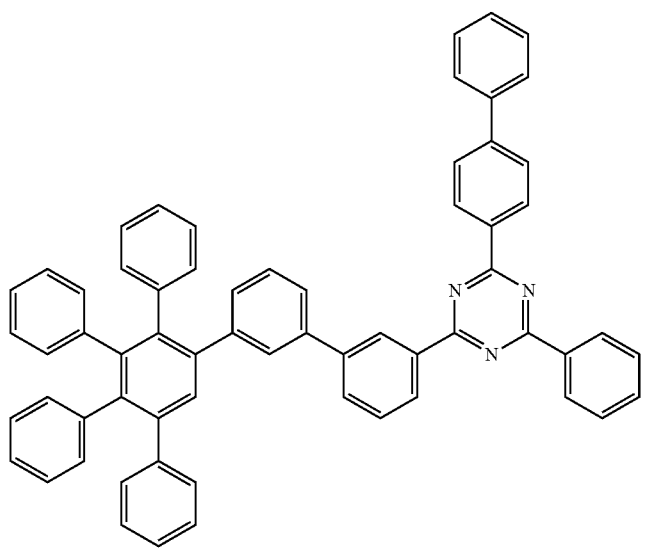
A5

A6
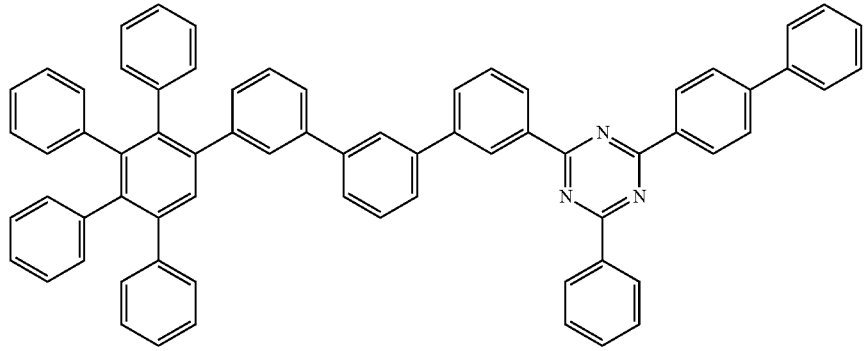
A7
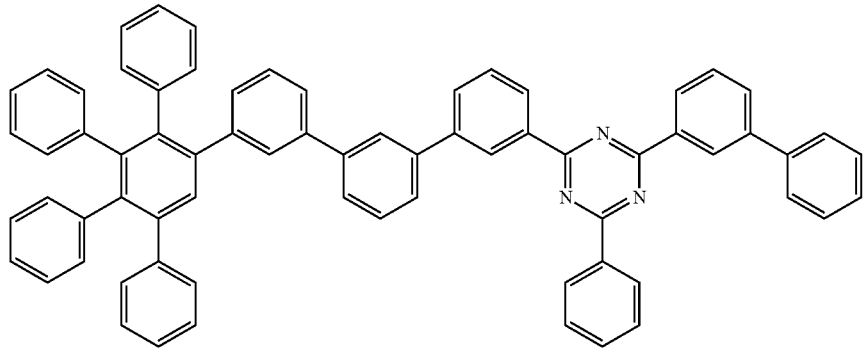
A8  A9
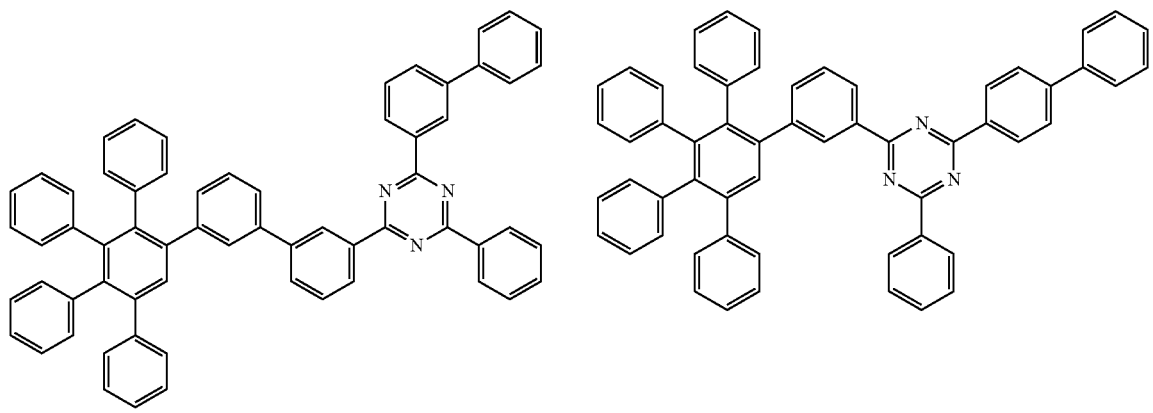
A10  A11
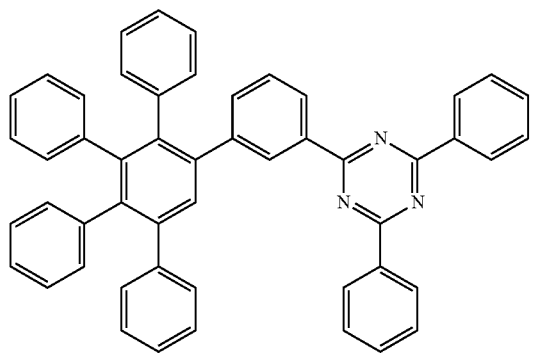
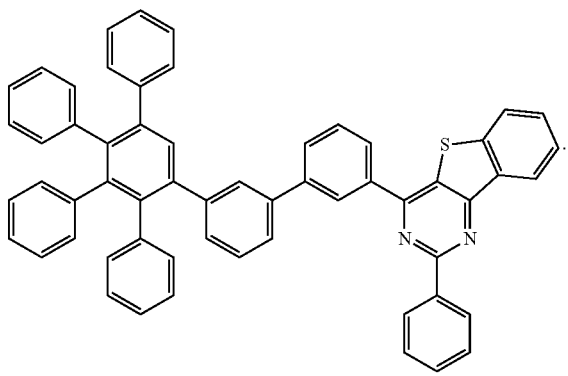

Second Electron Matrix Compound

According to a further aspect of the invention, in formula (II):

A-W$_f$ (II), wherein

A can be selected from the group of formula (IIIa) or (IIIb):

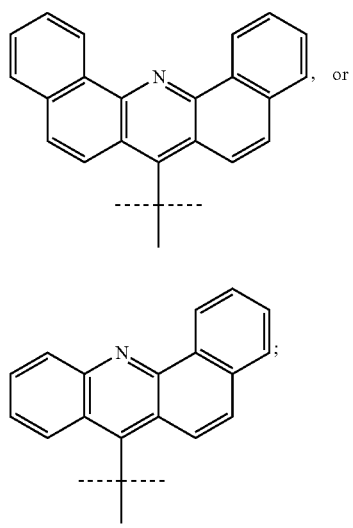

(IIIa)

(IIIb)

and

W can be independently selected from a substituted or unsubstituted $C_{16}$ to $C_{48}$ aryl group comprising 2 to 8 aromatic rings, and/or a substituted or unsubstituted $C_{10}$ to $C_{33}$ heteroaryl group comprising at least 2 to 8 aromatic rings; and the substituents are selected from deuterium, $C_1$ to $C_{12}$ alkyl and $C_1$ to $C_{12}$ alkoxy;

f can be 1 or 2, preferably f is 1.

Preferably, A can be selected from formula (IIIa).

According to a further aspect of the invention, W can be a substituted or unsubstituted $C_{16}$ to $C_{42}$ aryl group comprising 2 to 7 aromatic rings, or a substituted or unsubstituted $C_{10}$ to $C_{33}$ heteroaryl group comprising 2 to 7 aromatic rings; and preferably an unsubstituted $C_{12}$ to $C_{42}$ aryl group comprising 2 to 8 aromatic rings or 2 to 7 aromatic rings or 3 to 7 aromatic rings; or can be a substituted or unsubstituted $C_{12}$ to $C_{33}$ heteroaryl group comprising 2 to 8 aromatic rings; or an unsubstituted $C_{12}$ to $C_{33}$ heteroaryl group comprising 2 to 7 aromatic rings and 1 to 3 hetero atoms are N; or an unsubstituted $C_{18}$ to $C_{33}$ heteroaryl group comprising 3 to 7 aromatic rings and at least 1 to 3 hetero atoms are N.

According to a further aspect of the invention, W can be a substituted or unsubstituted $C_{10}$ to $C_{33}$ heteroaryl group comprising at least one organic ring of a diazole, a triazole, an azine, a diazine or a triazine.

According to a further aspect of the invention, in formula (II):

A-W$_f$ (II), wherein

A can be selected from the group of formula (IIIa) or (IIIb):

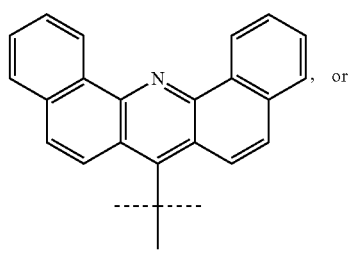

, or

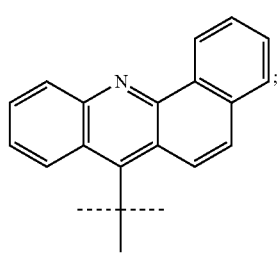

;

and

W can be independently selected from the group of formula IV:

-L-Ar$^2$ (IV); wherein

L is selected from phenylene, naphthylene and biphenylene; and

Ar$^2$ is selected from substituted or unsubstituted naphtyl, anthranyl, chrysenyl, pyrenyl, benzimidazolyl, pyridinyl, acridinyl, quinolinyl, triazinyl; and the substituents are selected from deuterium, $C_1$ to $C_{12}$ alkyl and $C_1$ to $C_{12}$ alkoxy;

f can be 1 or 2, preferably 1.

According to a further aspect of the invention, in formula (II):

A-W$_f$ (II), wherein

A is selected from the group of formula (IIIa) or (IIIb):

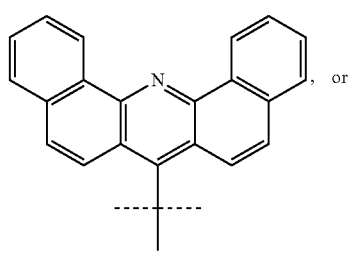

, or

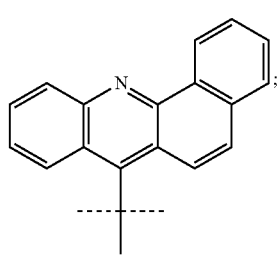

;

and

W is independently selected from the group of formula IV:

-L-Ar$^2$ (IV);

wherein

L is selected from phenylene and biphenylene; and

Ar² is selected from substituted or unsubstituted naphtyl, anthranyl, chrysenyl, pyrenyl, pyridinyl, acridinyl, quinolinyl; and the substituents are selected from deuterium, $C_1$ to $C_{12}$ alkyl and $C_1$ to $C_{12}$ alkoxy.

According to further aspect of the invention, W may be selected from the group of B1 to B55:

(B1)
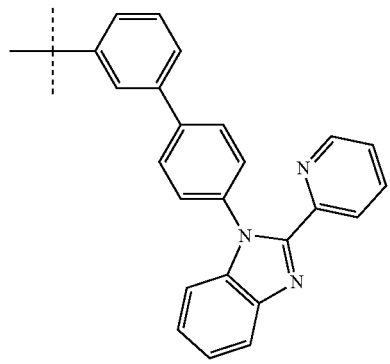

(B2)
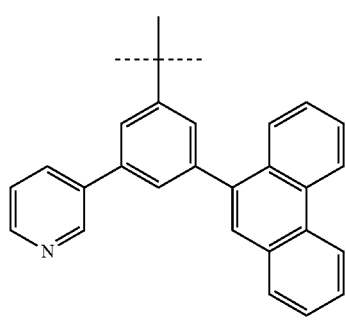

(B3)
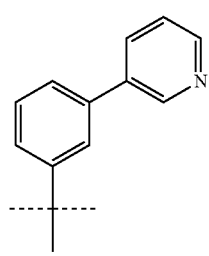

(B4)
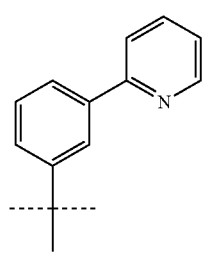

(B5)
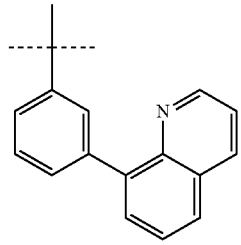

(B6)
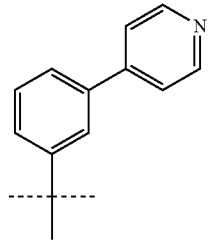

(B7)
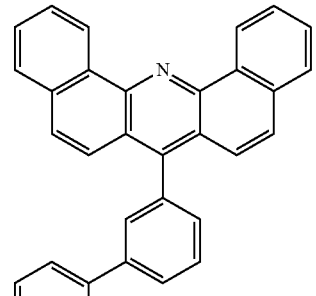

(B8)
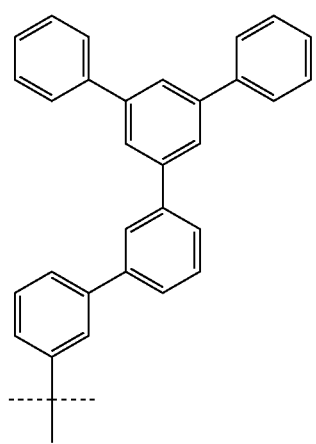

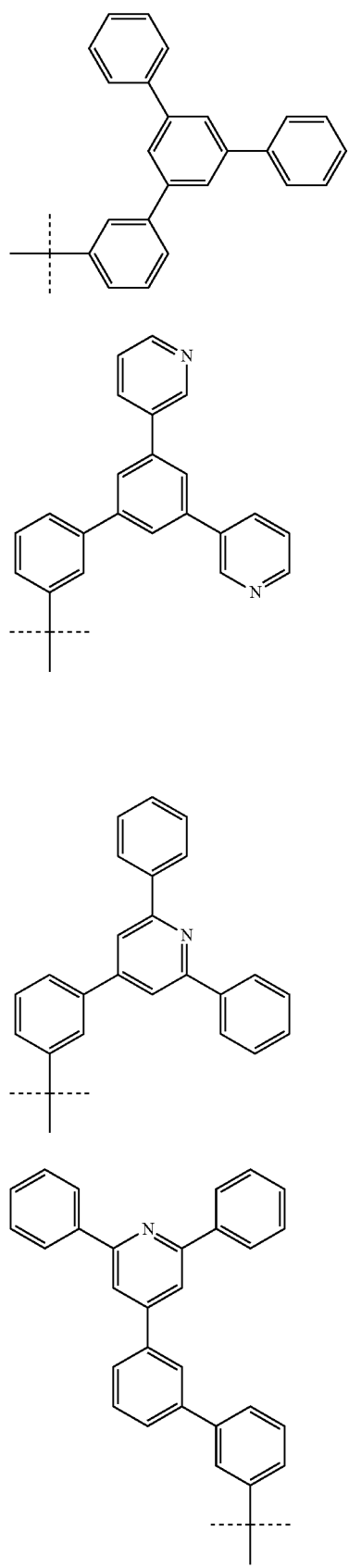
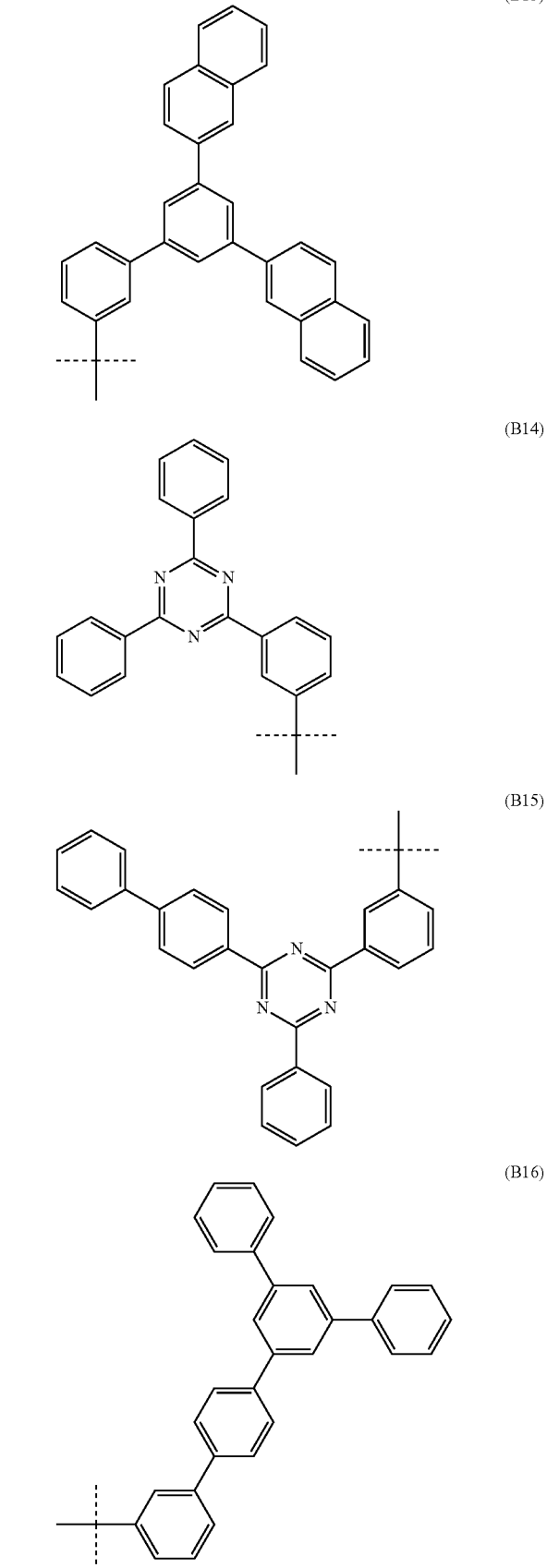

(B17)
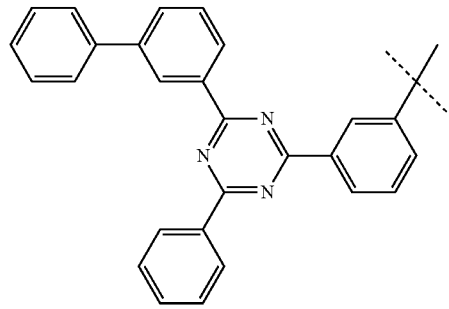
(B18)
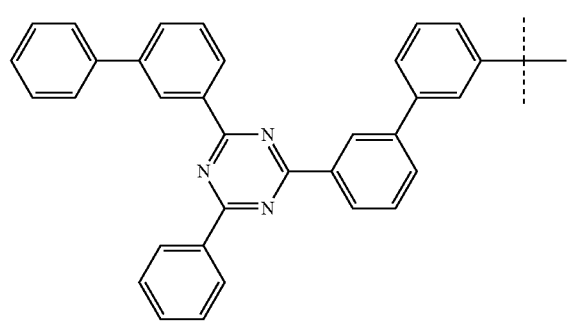
(B19)
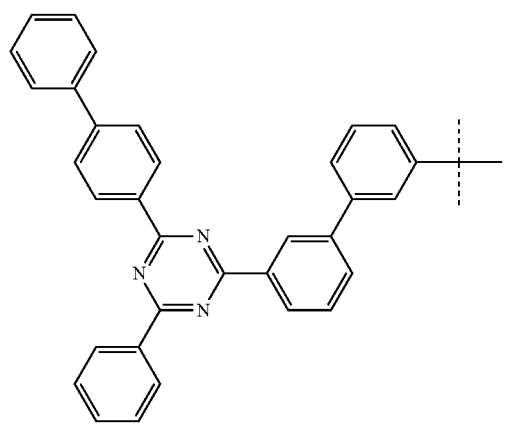
(B20)
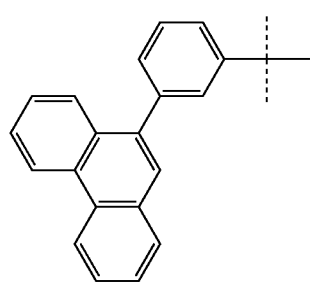
(B21)
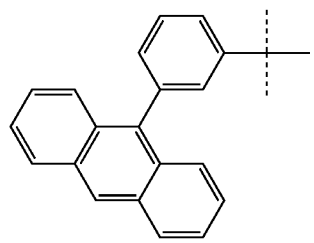
(B22)
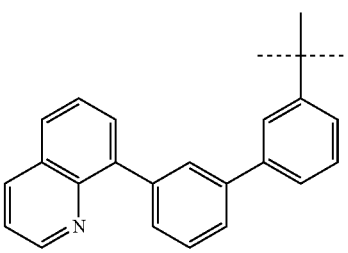
(B23)
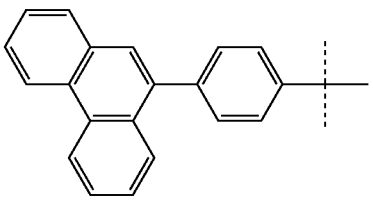
(B24)
(B25)
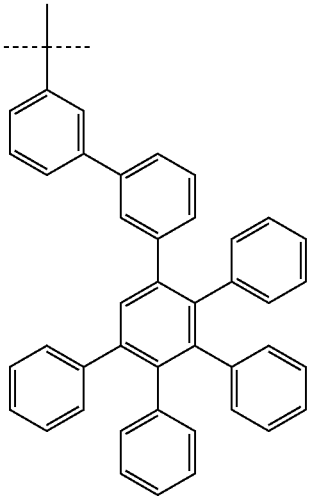

-continued
(B26)
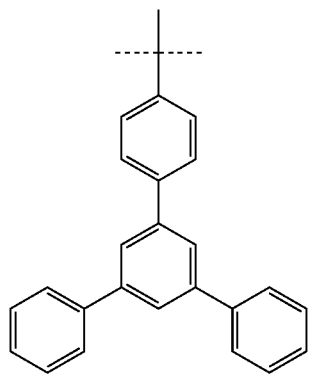
(B27)
(B28)
(B29)
(B30)
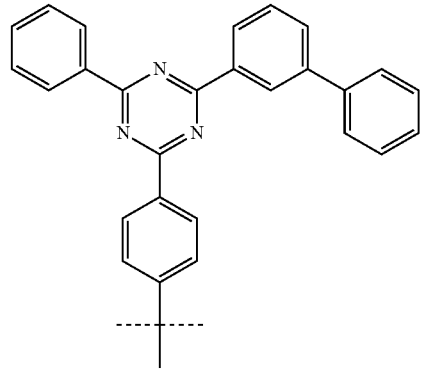
(B31)
(B32)
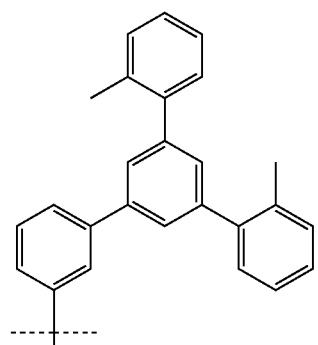
(B33)
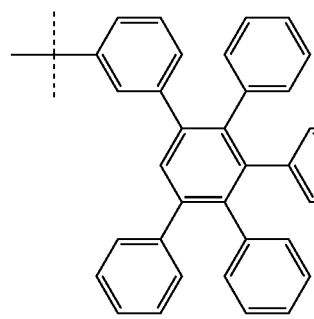

(B34)
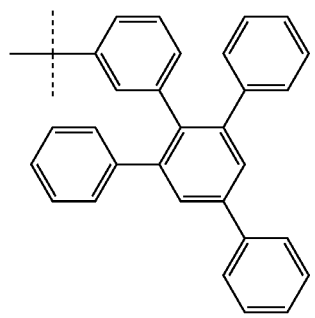
(B35)
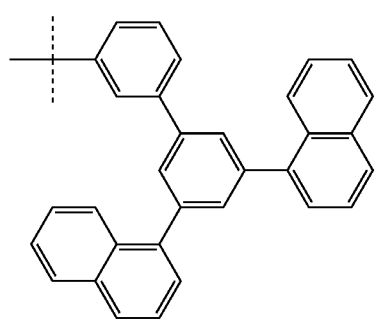
(B36)
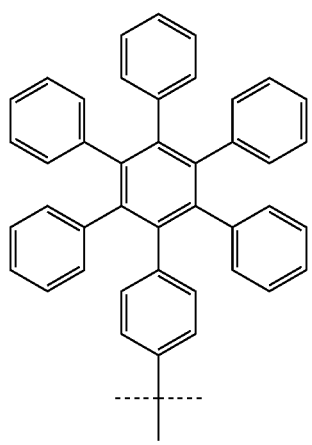
(B37)
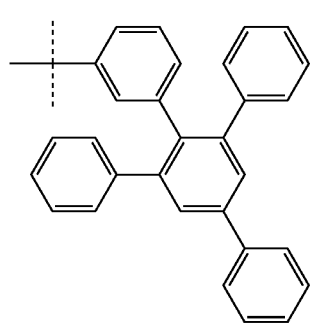
(B38)
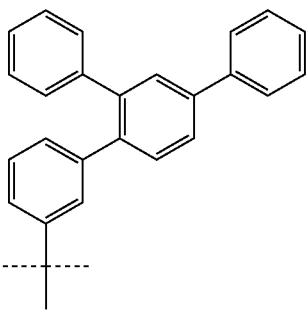
(B39)
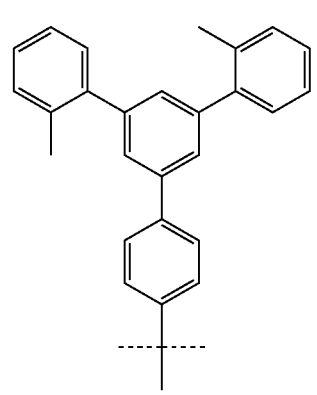
(B40)
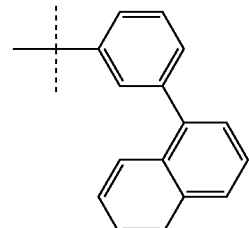
(B41)
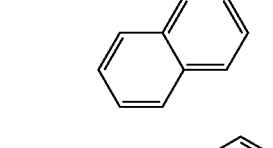
(B42)
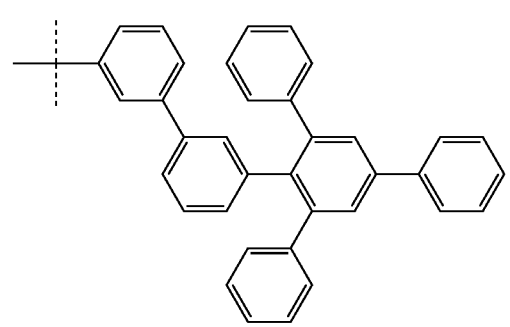

-continued
(B43) 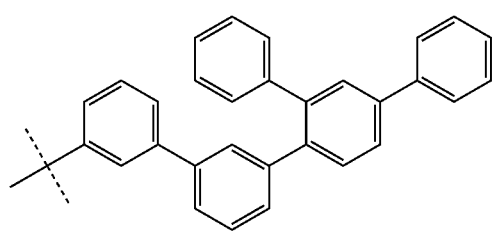
(B44) 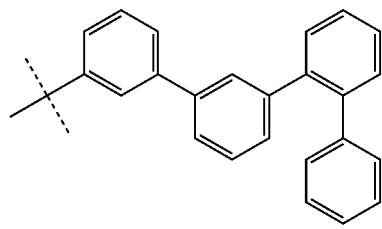
(B45) 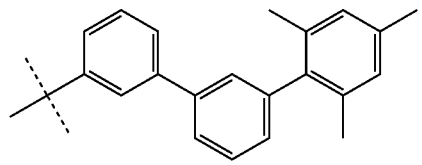
(B46) 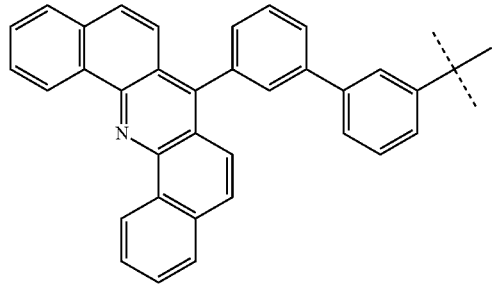
(B47) 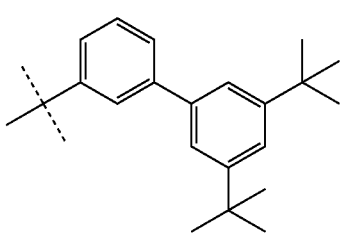
(B48) 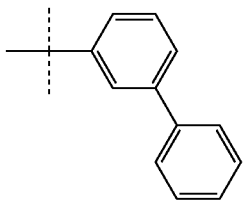
(B49) 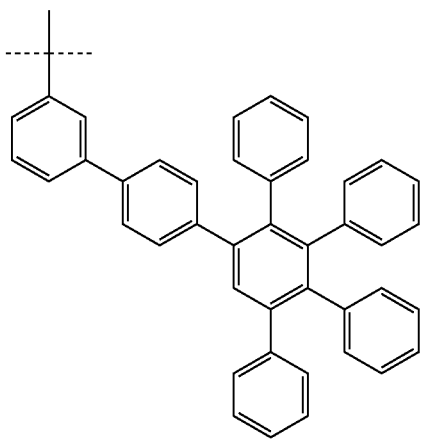
(B50) 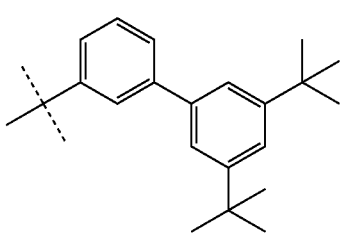
(B51) 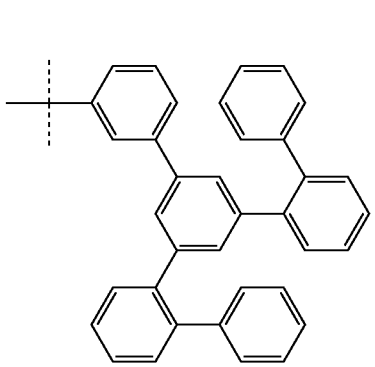
(B52) 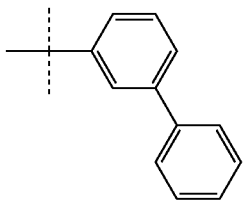
(B53) 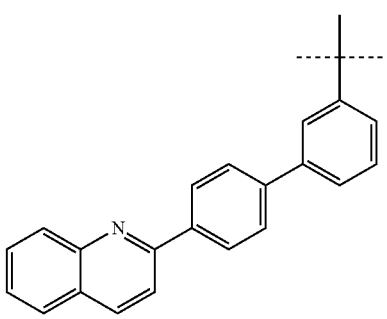

(B54)
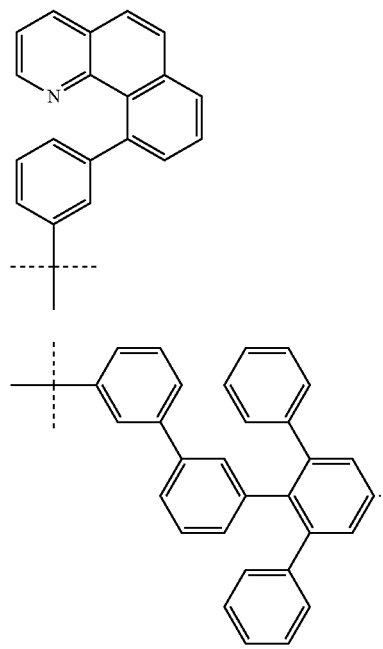
(B55)
According to a further aspect of the invention, the acridine derivative of Formula II may be selected from the group of matrix compounds (D1) to (D64):
(D1)
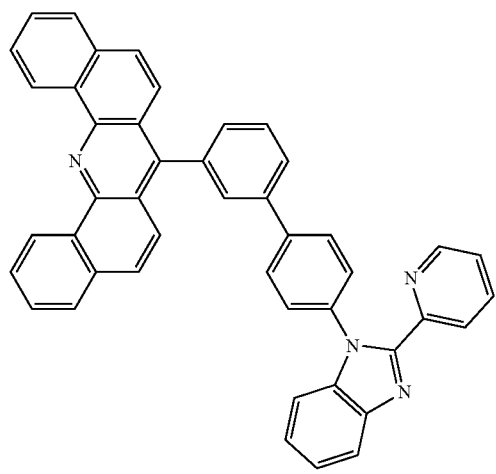
(D2)
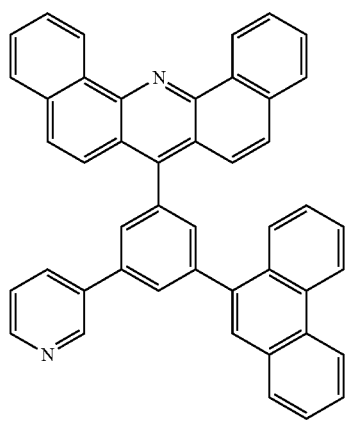
(D3)
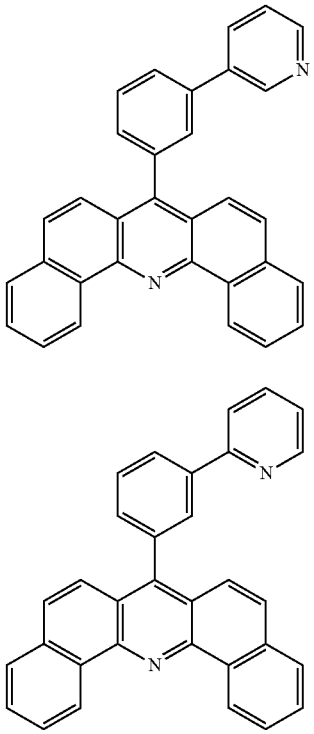
(D4)
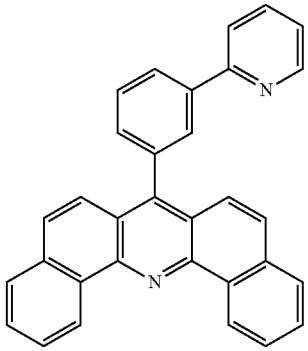
(D5)
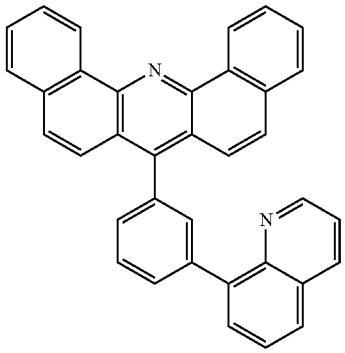
(D6)
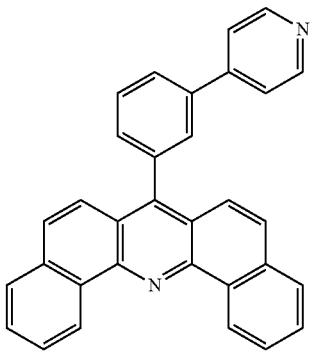

(D7)
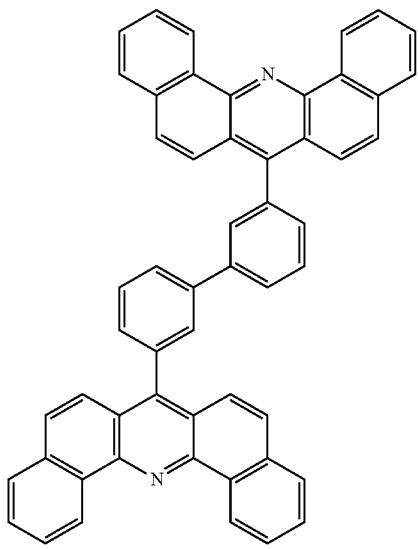
(D8)
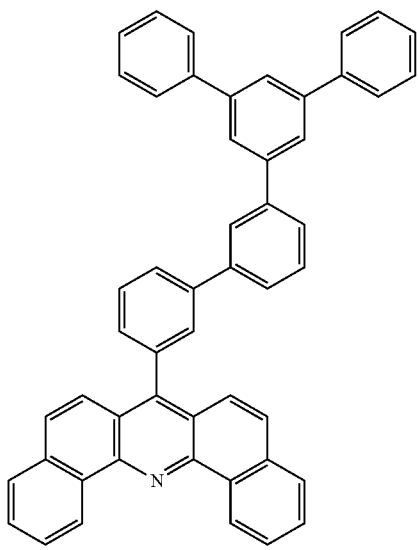
(D9)
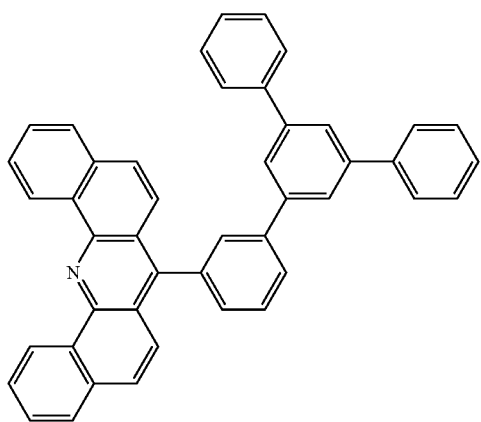
(D10)
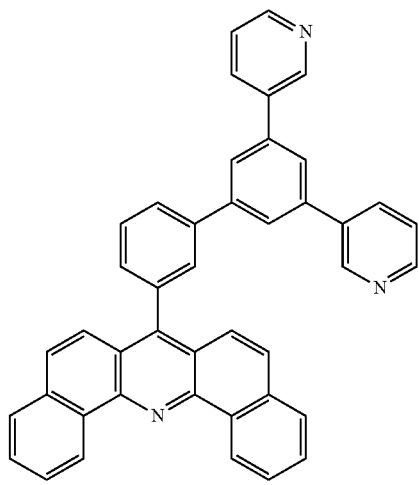
(D11)
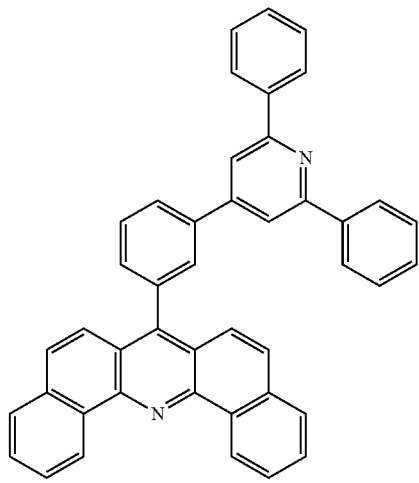
(D12)
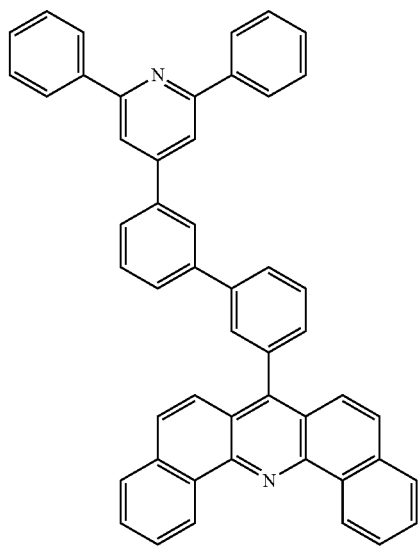

(D13)
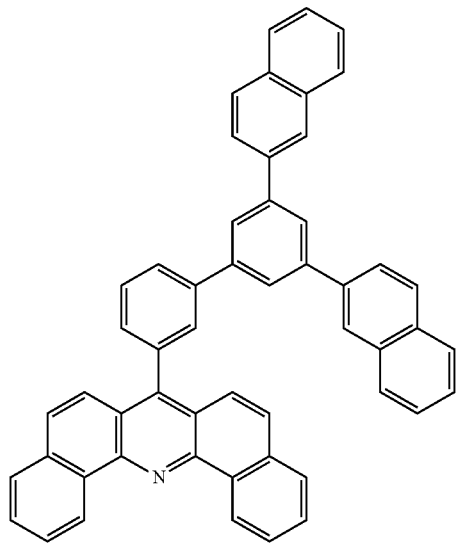
(D14)
(D15)
(D16)
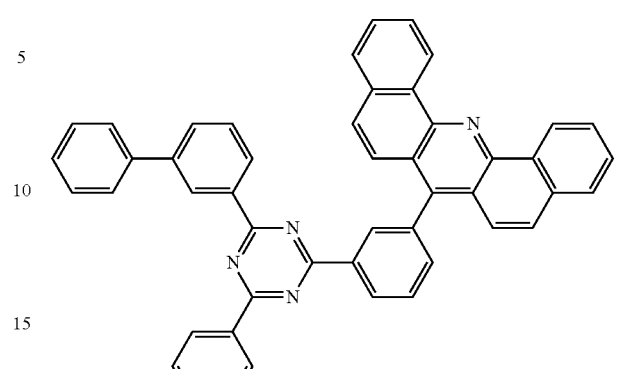
(D17)
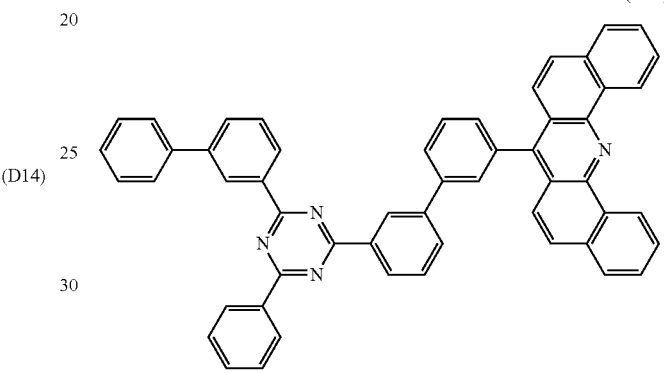
(D18)
(D19)
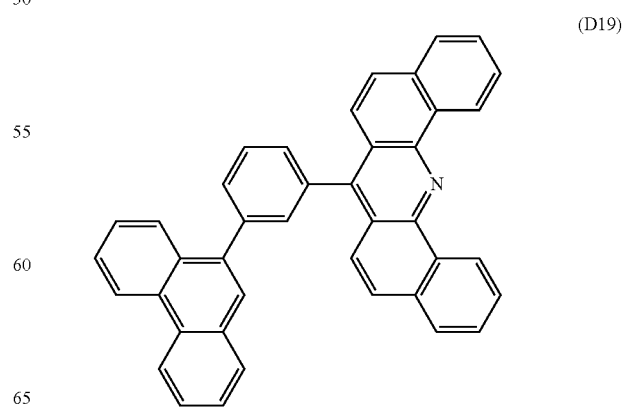

(D20)
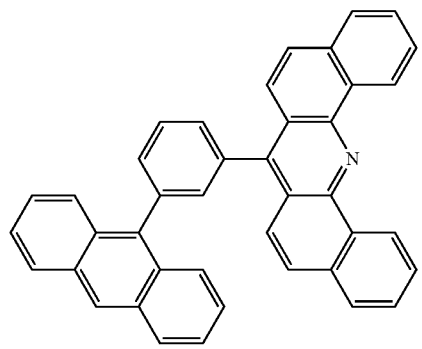
(D21)
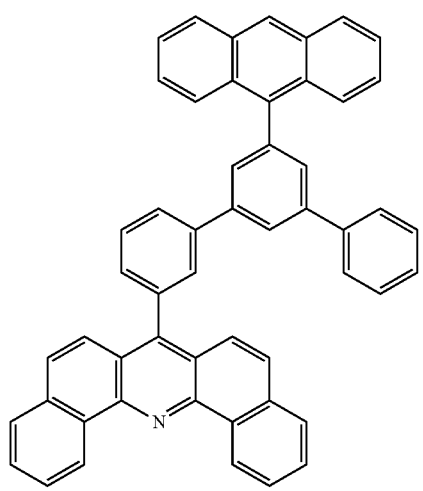
(D22)
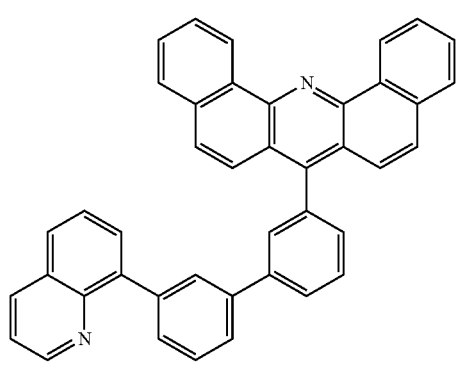
(D23)
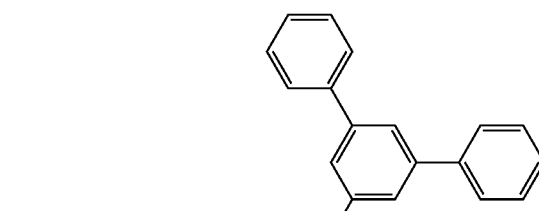
(D24)
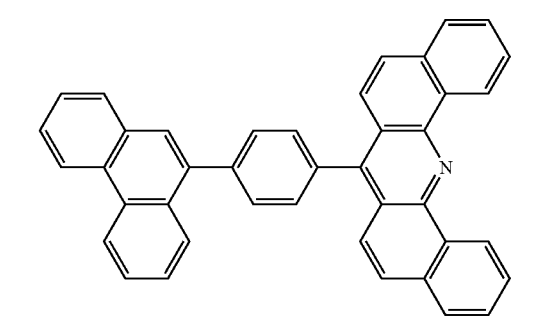
(D25)
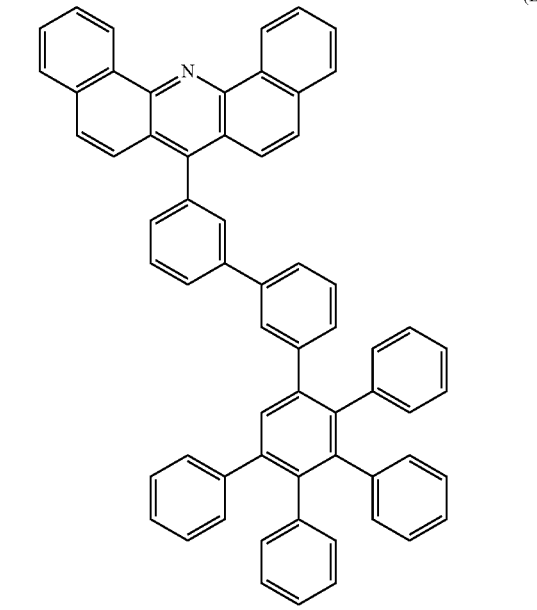

(D26)
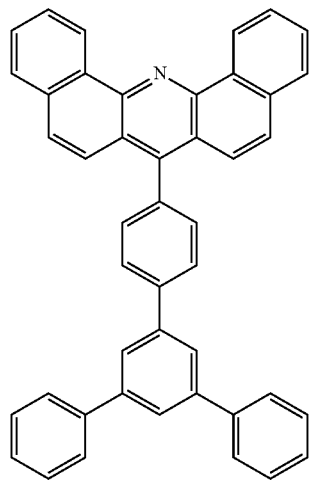
(D27)
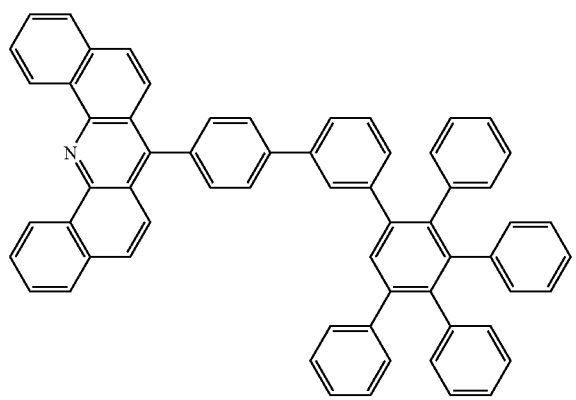
(D28)
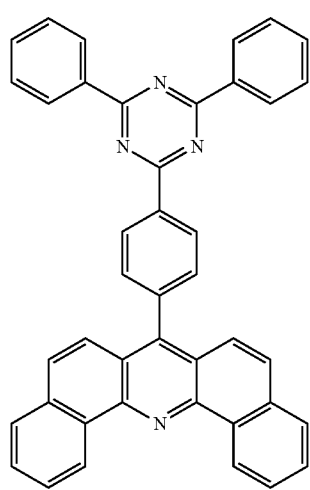
(D29)
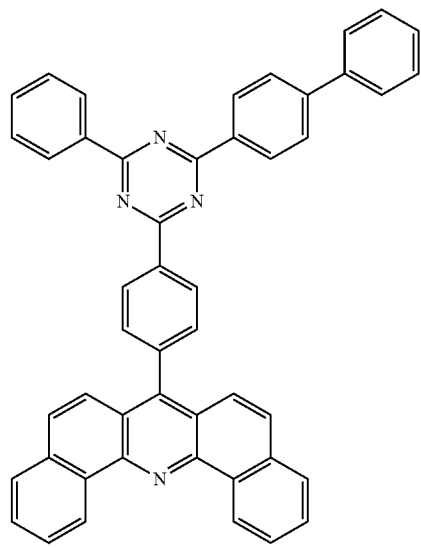
(D30)
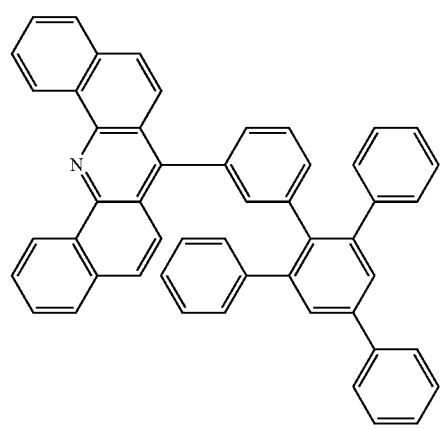
(D31)

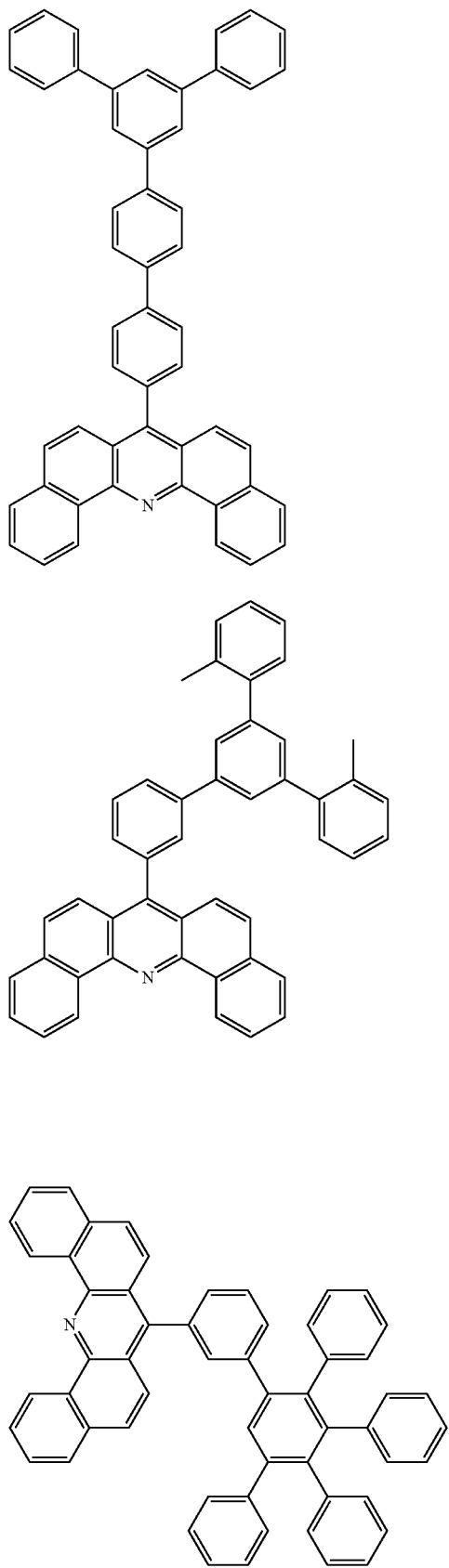
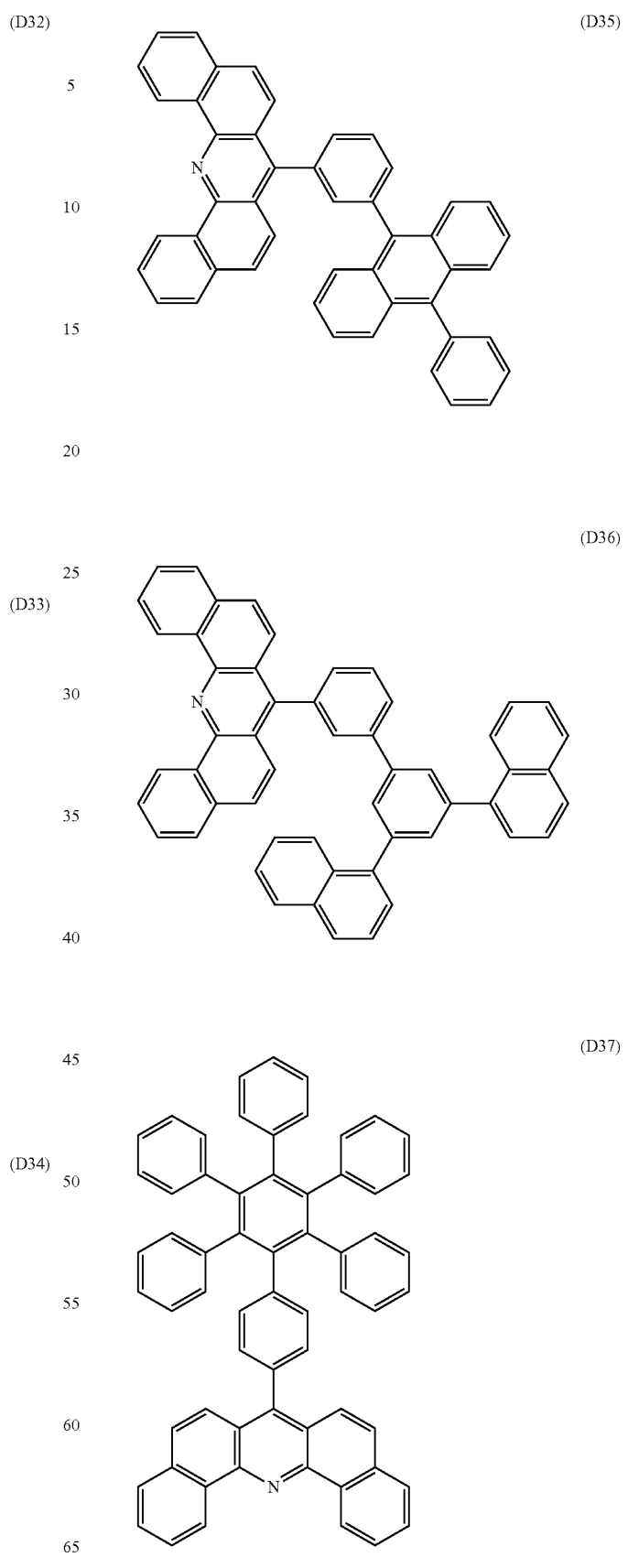

(D38)
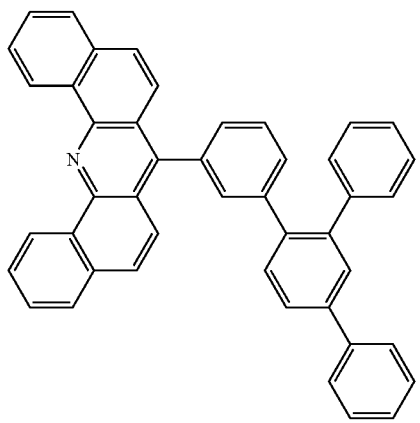
(D49)
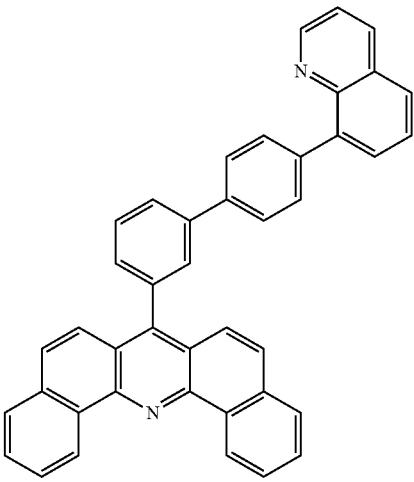
(D50)
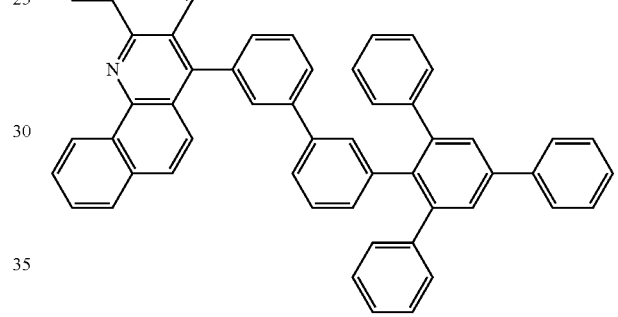
(D39)
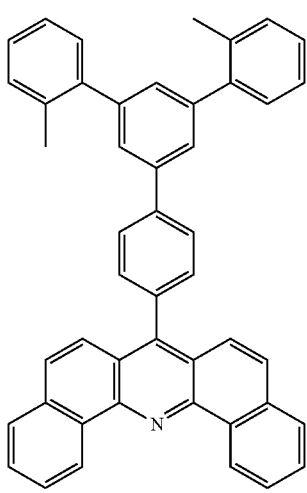
(D51)
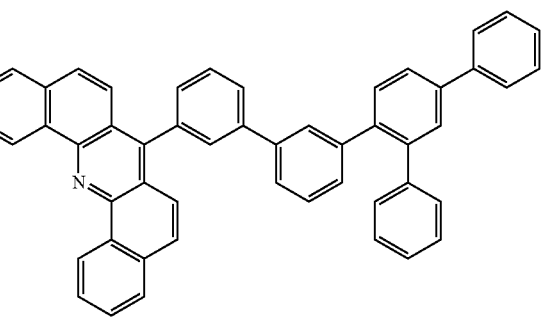
(D48)
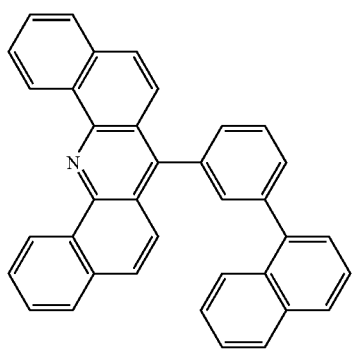
(D52)
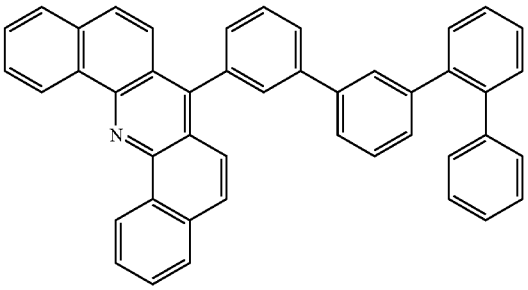

(D53)
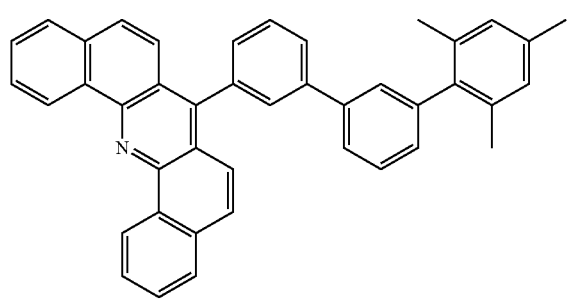
(D54)
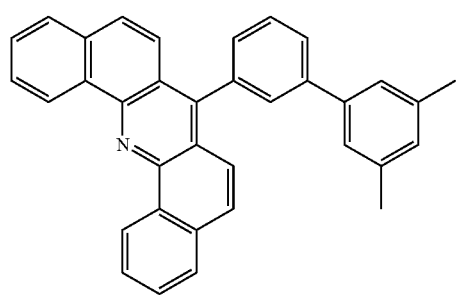
(D55)
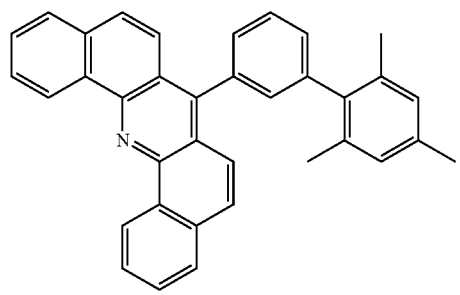
(D56)
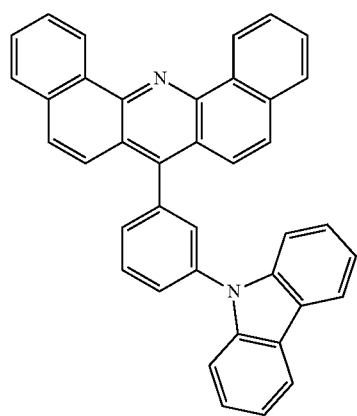
(D57)
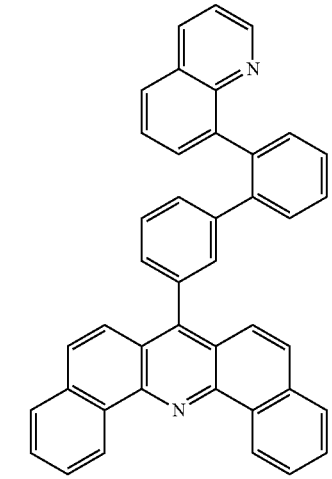
(D58)
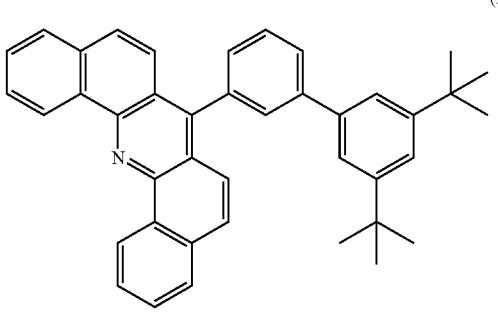
(D59)
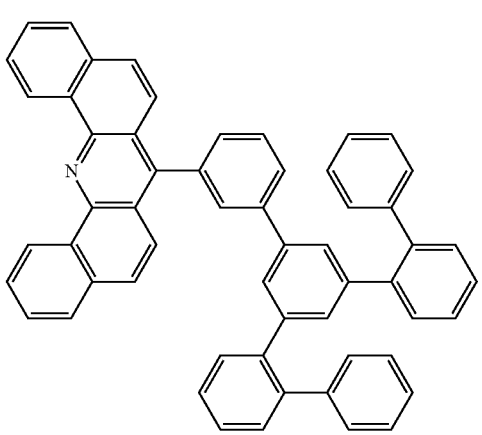
(D60)
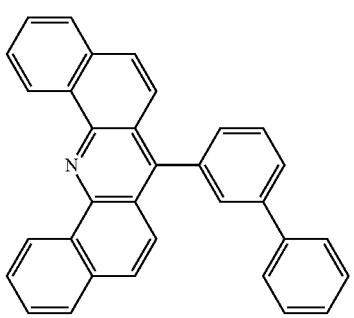

(D61)
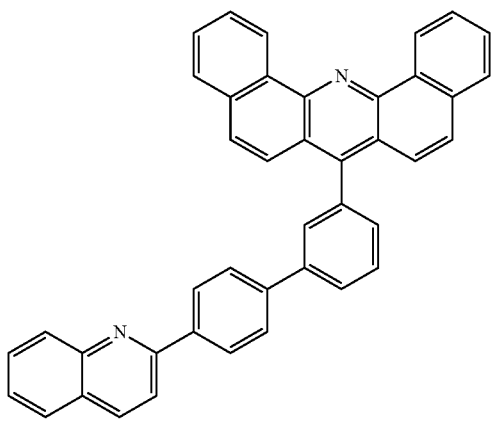

(D62)
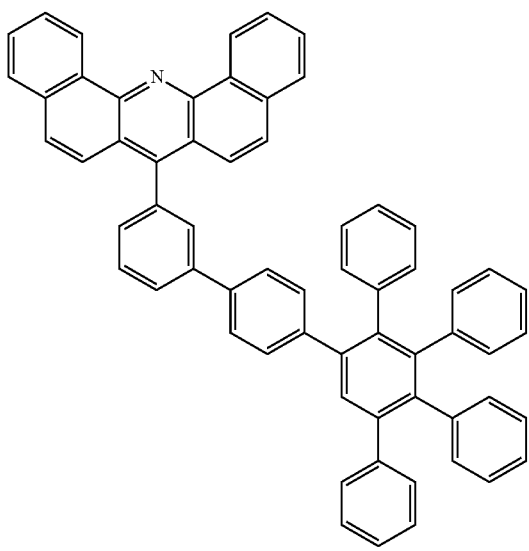

(D63)

(D64)
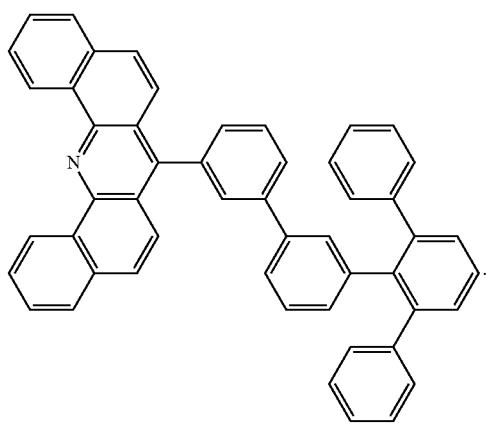

The compound of formula II may include at least 4 to about 15, preferably at least 5 to about 8, substituted or unsubstituted $C_6$ to $C_{18}$ aryl groups. Particularly good performance characteristics are obtained when the compound of formula II is selected in this range.

The compound of formula II may have a molecular weight (Mw) of ≥400 to ≤850 g/mol, preferably ≥450 to ≤830 g / mol. If the molecular weight is selected in this range, particularly reproducible evaporation and deposition can be achieved in vacuum at temperatures where good long-term stability is observed.

Preferably, the compound of formula II may be essentially non-emissive.

Preferably, the dipole moment of the compound of formula II may be selected ≥0 and ≤2.3 Debye, preferably ≥0.8 and ≤2.2 Debye, also preferred ≥1 and ≤2.2 Debye, also preferred ≥1.5 and ≤2.2 Debye. Particularly good performance is obtained when the compound of formula II is selected in this range.

Preferably, the first and/or the second electron transport matrix compound may have a dipole moment >0 and ≤2.3 Debye, preferably >0.2 and ≤2.2 Debye.

According to another aspect, the reduction potential of the compound of formula II may be selected more negative than −2.2 V and less negative than −2.35 V against Fc/Fc$^+$ in tetrahydrofuran, preferably more negative than −2.25 V and less negative than −2.3 V.

Alkali Metal Salt and Alkali Metal Organic Complex

According to a further aspect of the invention,
the alkali metal salt is selected from the group comprising LiF, LiCl, LiBr or LiJ, and preferably LiF;
the alkali metal organic complex is selected from the group comprising a lithium quinolinolate, lithium borate, lithium phenolate, lithium pyridinolate or comprises a lithium with a Schiff base ligand;
preferably the lithium quinolinolate complex has the formula IV, V or VI:

(IV)
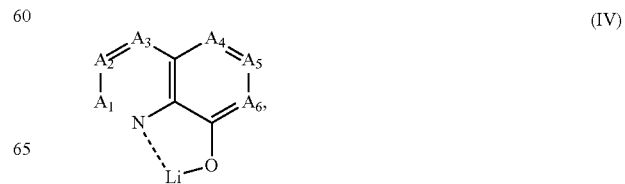

-continued

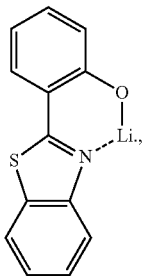

(V)

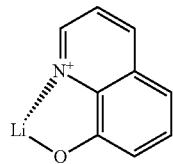

(VI)

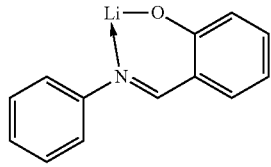
100

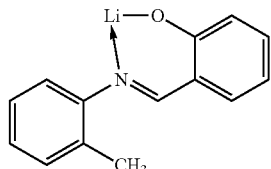
101

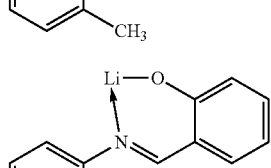
102

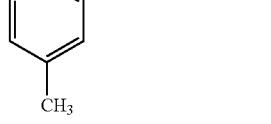
103 wherein
A1 to A6 are same or independently selected from CH, CR, N, O;
R is same or independently selected from hydrogen, halogen, alkyl or aryl or heteroaryl with 1 to 20 carbon atoms; and more preferred A1 to A6 are CH;
preferably the borate based organic ligand is a tetra(1H-pyrazol-1-yl)borate;
preferably the phenolate is a 2-(pyridin-2-yl)phenolate, a 2-(diphenylphosphoryl)phenolate, an imidazol phenolates, or 2-(pyridin-2-yl)phenolate and more preferred 2-(1-phenyl-1H-benzo[d]imidazol-2-yl)phenolate;
preferably the pyridinolate is a 2-(diphenylphosphoryl)pyridin-3-olate,
preferably the lithium Schiff base has the structure 100, 101, 102 or 103:

Extraordinary preferred may be lithium organic complexes, which may be used in the present invention are summarized in the following Table 1.

TABLE 1

| | Lithium organic complex that can be suitable used | | |
|---|---|---|---|
| Compound | Name | Structure | Disclosed in: |
| LiQ | lithium 8-hydroxyquinolate | | WO 2013079217 A1 |
| Li-1 | lithium tetra(1H-pyrazol-1-yl)borate | | WO 2013079676 A1 |

TABLE 1-continued

Lithium organic complex that can be suitable used

| Compound | Name | Structure | Disclosed in: |
|---|---|---|---|
| Li-2 | lithium 2-(diphenyl-phosphoryl)phenolate | 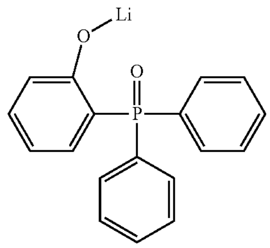 | WO 2013079678A1 |
| Li-3 | lithium 2-(pyridin-2-yl)phenolate | 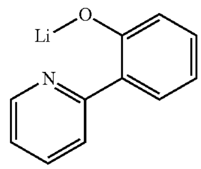 | JP2 008195623 |
| Li-4 | lithium 2-(1-phenyl-1H-benzo[d]imidazol-2-yl)phenolate | 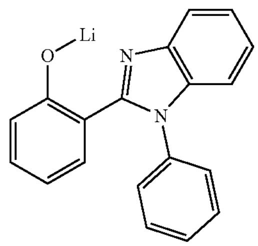 | JP 2001291593 |
| Li-5 | lithium 2-(benzo[d]oxazol-2-yl)phenolate | 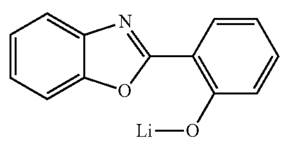 | US 20030165711 |
| Li-6 | lithium 2-(diphenyl-phosphoryl)pyridin-3-olate | 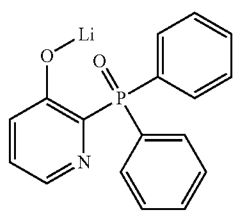 | EP 2724388 |

The alkali metal salt and alkali metal organic complex may be essentially non-emissive.

ETL Layer Stack

According to another embodiment, the first and the second matrix compound may be selected different, and wherein
the first electron transport layer consist of a first matrix compound of Chemical Formula (I); and
the second electron transport layer consist of a second matrix compound of Chemical Formula (II), and an alkali metal salt or an alkali metal organic complex.

The second electron transport layer is free of metals, transition metal organic complexes and organic n-dopants.

Preferably, the first and second electron transport layer may be essentially non-emissive.

According to another embodiment, the first electron transport layer can be in direct contact with the emission layer.

According to another embodiment, the first electron transport layer can be in direct contact with the second electron transport layer.

According to another embodiment, the first electron transport layer can be contacting sandwiched between the emission layer and the second electron transport layer.

According to another embodiment, the second electron transport layer can be in direct contact with the electron injection layer.

According to another embodiment, the second electron transport layer can be contacting sandwiched between the first electron transport layer and the electron injection layer.

According to another embodiment, the second electron transport layer can be in direct contact with the cathode electrode.

According to another embodiment, the second electron transport layer can be contacting sandwiched between the first electron transport layer and the cathode layer.

According to another embodiment, the first electron transport layer can be contacting sandwiched between the emission layer and the second electron transport layer, and the second electron transport layer can be contacting sandwiched between the first electron transport layer and the electron injection layer.

According to another aspect of the invention, the electronic device comprising at least one organic light emitting diode, preferably the electronic device is a display device.

According to another aspect of the invention, the organic electroluminescent device (300 or 400) can be an OLED.

The organic electroluminescent device may realize a low driving voltage, high efficiency, high luminance and long life-span by including a first and a second electron transport layer according to claim 1 in the organic electroluminescent device.

Figure 1:
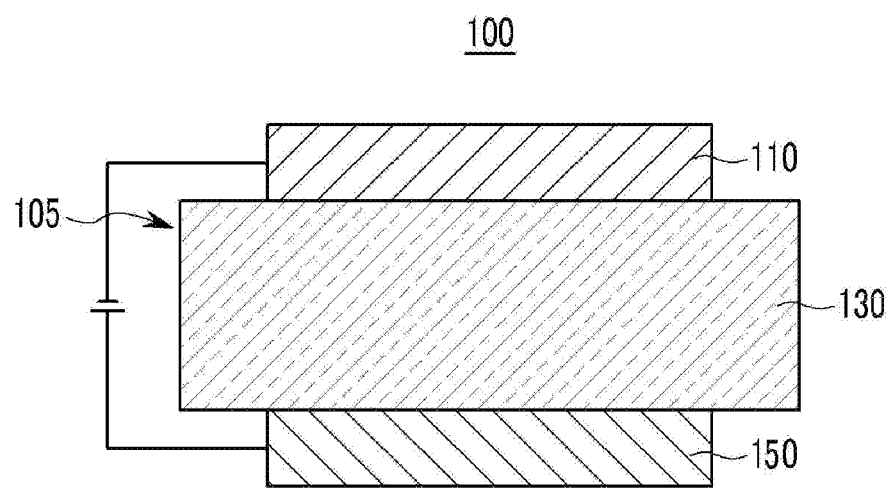
FIG. 1 is a cross-sectional view showing an organic light emitting diode according to an embodiment.

Hereinafter, the figures are illustrated in more detail with reference to examples. However, the present disclosure is not limited to the following figures.

FIGS. 1 to 4 are schematic cross-sectional views of organic light emitting diodes 100, 200, 300, and 400 according to an embodiment of the present invention. Hereinafter, referring to FIG. 1, a structure of an organic light emitting diode according to an embodiment of the present invention and a method of manufacturing the same are as follows. The organic light emitting diode 100 has a structure where a cathode 110, an organic layer 105 including an optional hole transport region; an emission layer 130; and an anode 150 that are sequentially stacked.

A substrate may be further disposed under the cathode 110 or on the anode 150. The substrate may be a substrate that used in a general organic light emitting diode and may be a glass substrate or a transparent plastic substrate with strong mechanical strength, thermal stability, transparency, surface smoothness, ease of handling, and water resistance.

The anode 150 may be formed by depositing or sputtering an anode material on a substrate. The anode material may be selected from materials having a high work function that makes hole injection easy. The anode 150 may be a reflective electrode, a transflective electrode, or a transmissive electrode. The anode material may use indium tin oxide (ITO), indium zinc oxide (IZO), tin oxide ($SnO_2$), zinc oxide (ZnO), and the like. Or, it may be a metal such as magnesium (Mg), aluminum (Al), aluminum-lithium (Al—Li), calcium (Ca), magnesium-indium (Mg—In), or magnesium-silver (Mg—Ag).

The anode 150 may have a monolayer or a multi-layer structure of two or more layers.

The organic light emitting diodes 100, 200, 300, and 400 according to an embodiment of the present invention may include a hole transport region; an emission layer 120; and an first electron transport layer 135 comprising a compound according to formula I.

Figure 2:
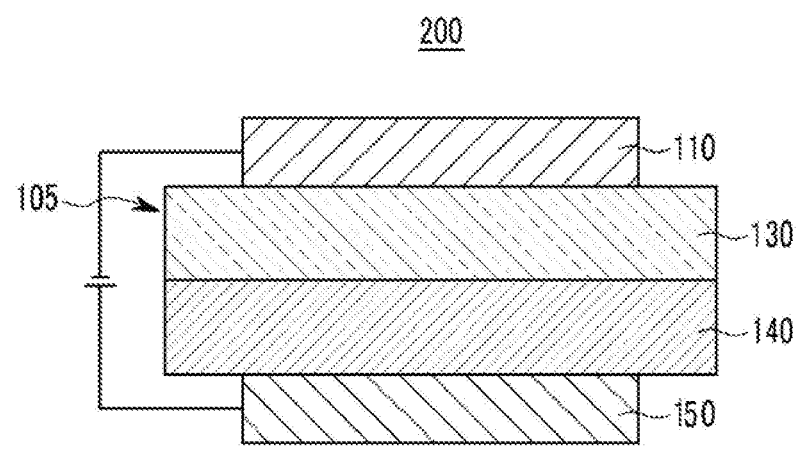
FIG. 2 is a cross-sectional view specifically showing an organic layer of an organic light emitting diode according to an embodiment.

For example, referring to FIG. 2, an organic light emitting diode according to an embodiment of the present invention is described. The organic light emitting diodes 100, 200, 300, and 400 according to an embodiment of the present invention may include further a hole auxiliary layer 140 between the anode 120 and the emission layer 130.

Figure 3:
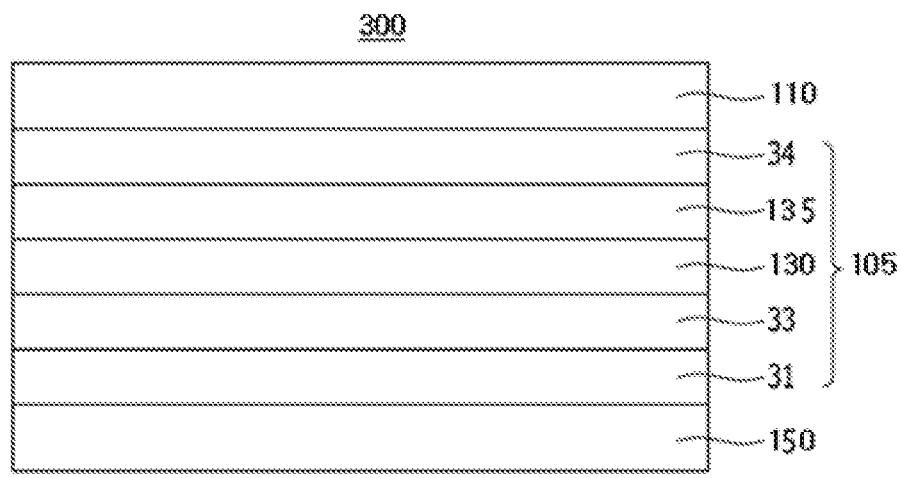
FIGS. 3 and 4 are cross-sectional views specifically showing a part of an organic layer of an organic light emitting diode according to an embodiment.

Referring to FIG. 3, the hole transport region 105 may include at least two layered hole auxiliary layer, and in this case, a hole auxiliary layer contacting the emission layer is defined as a electron blocking layer 33 and a hole auxiliary layer contacting an anode is defined as a hole transport layer 31 as well as two electron transport layers, namely first electron transport layer 35 and the second electron transport layer 34. The hole transport region may include at least one of a hole injection layer, a hole transport layer, an electron blocking layer, and a buffer layer.

The hole transport region may include only hole injection layer or only hole transport layer. Or, the hole transport region may have a structure where a hole injection layer 37/hole transport layer 31 or hole injection layer 37/hole transport layer 31/electron blocking layer is sequentially stacked from the anode 120.

Figure 4:
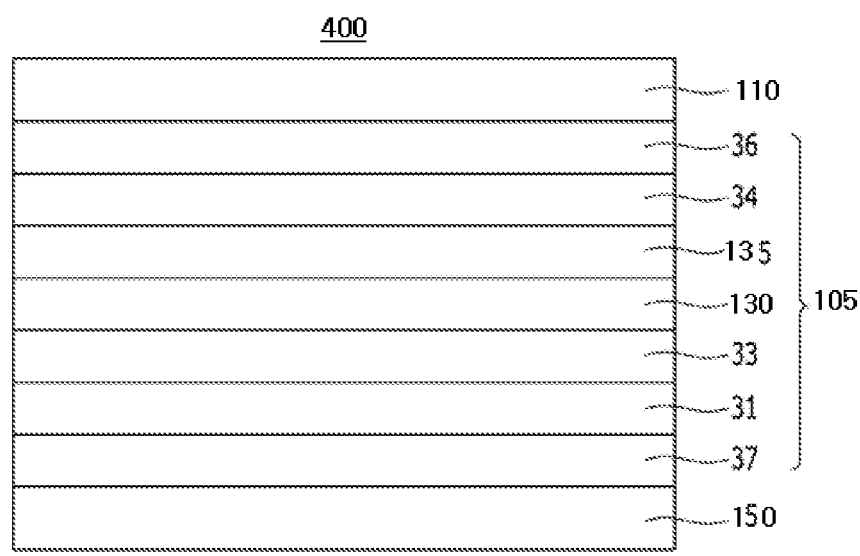

For example, the hole injection layer 37 and the electron injection layer 36 are additionally included and as shown in FIG. 4, anode 120/hole injection layer 37/hole transport layer 31/electron blocking layer 33/emission layer 130/first electron transport layer 135/ second electron transport layer 34/electron injection layer 37/anode 110 are sequentially stacked.

According to another aspect of the invention, the organic electroluminescent device (400) comprises an anode (150), a hole injection layer (37), a hole transport layer (31), optional an electron blocking layer (33), an emission layer (130), first electron transport layer (135), second electron transport layer (34), an optional electron injection layer (34), a cathode (110) wherein the layers are arranged in that order.

The hole injection layer 37 may improve interface properties between ITO as an anode and an organic material used for the hole transport layer 31, and is applied on a non-planarized ITO and thus planarizes the surface of the ITO. For example, the hole injection layer 37 may include a material having a median value, particularly desirable conductivity between a work function of ITO and HOMO of the hole transport layer 31, in order to adjust a difference a work function of ITO as an anode and HOMO of the hole transport layer 31.

When the hole transport region includes a hole injection layer 37, the hole injection layer may be formed on the anode 150 by any of a variety of methods, for example, vacuum deposition, spin coating, casting, Langmuir-Blodgett (LB) method, or the like.

When hole injection layer is formed using vacuum deposition, vacuum deposition conditions may vary depending on the material that is used to form the hole injection layer, and the desired structure and thermal properties of the hole injection layer to be formed and for example, vacuum deposition may be performed at a temperature of about 100° C. to about 500° C., a pressure of about $10^{-8}$ torr to about $10^{-3}$ torr, and a deposition rate of about 0.01 to about 100 Å/sec, but the deposition conditions are not limited thereto.

When the hole injection layer is formed using spin coating, the coating conditions may vary depending on the material that is used to form the hole injection layer, and the desired structure and thermal properties of the hole injection layer to be formed. For example, the coating rate may be in the range of about 2000 rpm to about 5000 rpm, and a temperature at which heat treatment is performed to remove a solvent after coating may be in a range of about 80° C. to about 200° C., but the coating conditions are not limited thereto.

Conditions for forming the hole transport layer and the electron blocking layer may be defined based on the above-described formation conditions for the hole injection layer.

A thickness of the hole transport region may be from about 100 Å to about 10000 Å, for example, about 100 Å to about 1000 Å. When the hole transport region includes the hole injection layer and the hole transport layer, a thickness of the hole injection layer may be from about 100 Å to about 10,000 Å, for example about 100 Å to about 1000 Å and a thickness of the hole transport layer may be from about 50 Å to about 2,000 Å, for example about 100 Å to about 1500 Å. When the thicknesses of the hole transport region, the HIL, and the HTL are within these ranges, satisfactory hole transport characteristics may be obtained without a substantial increase in driving voltage.

The hole transport region may further include a charge-generating material to improve conductivity, in addition to the materials as described above. The charge-generating material may be homogeneously or non-homogeneously dispersed in the hole transport region. The charge-generating material may be, for example, a p-dopant. The p-dopant may be one of a quinine derivative, a metal oxide, and a cyano group-containing compound, but is not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as compound HT-D1 below.

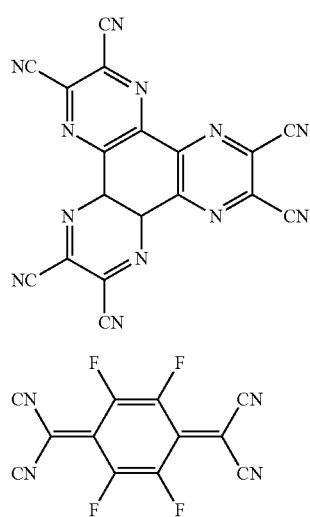

Compound HT-D1

F4-TCNQ

The hole transport region may further include a buffer layer.

The buffer layer may compensate for an optical resonance distance of light according to a wavelength of the light emitted from the EML, and thus may increase efficiency.

The emission layer (EML) may be formed on the hole transport region by using vacuum deposition, spin coating, casting, LB method, or the like. When the emission layer is formed using vacuum deposition or spin coating, the conditions for deposition and coating may be similar to those for the formation of the hole injection layer, though the conditions for the deposition and coating may vary depending on the material that is used to form the emission layer. The emission layer may include an emitter host (EML host) and a dopant.

The dopant may be a red, green, or blue dopant.

Preferably, the emitter host is an anthracene matrix compound represented by Formula 400 below:

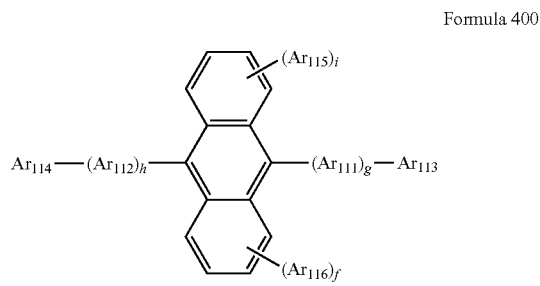

Formula 400

In Formula 400, $Ar_{111}$ and $Ar_{112}$ may be each independently a substituted or unsubstituted $C_6$-$C_{60}$ arylene group; $Ar_{113}$ to $Ar_{116}$ may be each independently a substituted or unsubstituted $C_1$-$C_{10}$ alkyl group or a substituted or unsubstituted $C_6$-$C_{60}$ aryl group; and g, h, i, and j may be each independently an integer from 0 to 4. In some embodiments, $Ar_{111}$ and $Ar_{112}$ in Formula 400 may be each independently one of a phenylene group, a naphthylene group, a phenanthrenylene group, or a pyrenylene group; or a phenylene group, a naphthylene group, a phenanthrenylene group, a fluorenyl group, or a pyrenylene group, each substituted with at least one of a phenyl group, a naphthyl group, or an anthryl group.

In Formula 400, g, h, i, and j may be each independently an integer of 0, 1, or 2. In Formula 400, $Ar_{113}$ to $Ar_{116}$ may be each independently one of a $C_1$-$C_{10}$ alkyl group substituted with at least one of a phenyl group, a naphthyl group, or an anthryl group;

a phenyl group, a naphthyl group, an anthryl group, a pyrenyl group, a phenanthrenyl group, or a fluorenyl group;

a phenyl group, a naphthyl group, an anthryl group, a pyrenyl group, a phenanthrenyl group, or a fluorenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, or a fluorenyl group; or

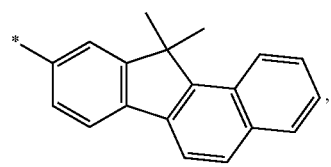 [SMILES: *c1ccc2c(c1)C(C)(C)c1c-2ccc2ccccc12]

or formulas (Y2) or (Y3)

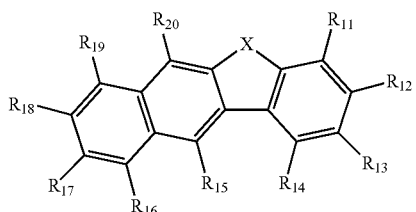
(2)

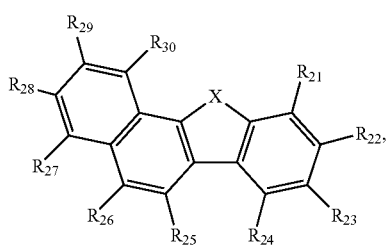
(3)

Wherein in the formulas (Y2) and (Y3), X is selected form an oxygen atom and a sulfur atom, but embodiments of the invention are not limited thereto.

In the formula (Y2), any one of $R_{11}$ to $R_{14}$ is used for bonding to $Ar_{111}$. $R_{11}$ to $R_{14}$ that are not used for bonding to $Ar_{111}$ and $R_{15}$ to $R_{20}$ are the same as $R_1$ to $R_8$.

In the formula (Y3), any one of $R_{21}$ to $R_{24}$ is used for bonding to $Ar_{111}$. $R_{21}$ to $R_{24}$ that are not used for bonding to $A_{111}$ and $R_{25}$ to $R_{30}$ are the same as $R_1$ to $R_8$.

Preferably, the EML host comprises between one and three heteroatoms selected from the group consisting of N, O or S. More preferred the EML host comprises one heteroatom selected from S or O.

Preferably, the dipole moment of the EML host can be selected $\geq 0.2$ Debye and $\leq 1.45$ Debye, preferably $\geq 0.4$ Debye and $\leq 1.2$ Debye, also preferred $\geq 0.6$ Debye and $\leq 1.1$ Debye.

The dipole moment is calculated using the optimized using the hybrid functional B3LYP with the 6-31G* basis set as implemented in the program package TURBOMOLE V6.5. If more than one conformation is viable, the conformation with the lowest total energy is selected to determine the dipole moment of the molecules. Using this method, 2-(10-phenyl-9-anthracenyl)-benzo[b]naphtho[2,3-d]furan (CAS 1627916-48-6) has a dipole moment of 0.88 Debye, 2-(6-(10-phenylanthracen-9-yl) naphthalen-2-yl)dibenzo[b,d]thiophene (CAS 1838604-62-8) of 0.89 Debye, 2-(6-(10-phenylanthracen-9-yl)naphthalen-2-yl)dibenzo[b,d]furan (CAS 1842354-89-5) of 0.69 Debye, 2-(7-(phenanthren-9-yl)tetraphen-12-yl)dibenzo[b,d]furan (CAS 1965338-95-7) of 0.64 Debye, 4-(4-(7-(naphthalen-1-yl)tetraphen-12-yl)phenyl)dibenzo[b,d]furan (CAS 1965338-96-8) of 1.01 Debye.

According to a further aspect of the invention, the emitter host respectively has a reduction potential which, if measured under the same conditions by cyclic voltammetry against Fc/Fc$^+$ in tetrahydrofuran, has a value more negative than the respective value obtained for 7-([1,1'-biphenyl]-4-yl)dibenzo[c,h]acridine, preferably more negative than the respective value for 9,9',10,10'-tetraphenyl-2,2'-bianthracene, more preferably more negative than the respective value for 2,9-di([1,1'-biphenyl]-4-yl)-4,7-diphenyl-1,10-phenanthroline, even more preferably more negative than the respective value for 2,4,7,9-tetraphenyl-1,10-phenanthroline, even more preferably more negative than the respective value for 9,10-di(naphthalen-2-yl)-2-phenylanthracene, even more preferably more negative than the respective value for 2,9-bis(2-methoxyphenyl)-4,7-diphenyl-1,10-phenanthroline, most preferably more negative than the respective value for 9,9'-spirobi[fluorene]-2,7-diyl-bis(diphenylphosphine oxide).

The dopant is mixed in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The dopant may be a fluorescent dopant, for example ter-fluorene, the structures are shown below. 4.4'-bis(4-diphenyl amiostyryl)biphenyl (DPAVBi), 2,5,8,11-tetra-tert-butyl perylene (TBPe), and Compound 4 below are examples of fluorescent blue dopants.

Compound 4

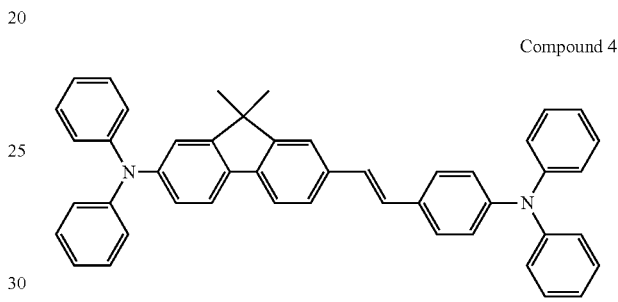

According to another aspect, the organic semiconductor layer comprising a compound of formula II is arranged between a fluorescent blue emission layer and the cathode electrode.

The dopant may be a phosphorescent dopant, and examples of the phosphorescent dopant may be an organic metal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by Chemical Formula Z, but is not limited thereto:

$$L_2MX \qquad (Z).$$

In Chemical Formula Z, M is a metal, and L and X are the same or different, and are a ligand to form a complex compound with M.

The M may be, for example Ir, Pt, Os, Ti, Zr, Hf, Eu, Tb, Tm, Fe, Co, Ni, Ru, Rh, Pd or a combination thereof, and the L and X may be, for example a bidendate ligand.

A thickness of the emission layer may be about 100 Å to about 1000 Å, for example about 200 Å to about 600 Å. When the thickness of the emission layer is within these ranges, the emission layer may have improved emission characteristics without a substantial increase in a driving voltage.

Next, an electron transport region is disposed on the emission layer.

The electron transport region may include at least one of a first electron transport layer, an electron transport layer, and an electron injection layer.

For example, the electron transport region may have a structure of a first electron transport layer/electron transport layer/electron injection layer or electron transport layer/electron injection layer, but is not limited thereto. For example, an organic light emitting diode according to an embodiment of the present invention includes at least two electron transport layers in the electron transport region, and in this case, an electron transport layer contacting the emission layer is defined as a first electron transport layer 135.

The electron transport layer may have a monolayer or multi-layer structure including two or more different materials.

The formation conditions of the first electron transport layer 135, second electron transport layer 34, and electron injection layer 36 of the electron transport region refers to the formation condition of the hole injection layer.

The thickness of the first electron transport layer may be from about 20 Å to about 1000 Å, for example about 30 Å to about 300 Å. When the thickness of the first electron transport layer is within these ranges, the first electron transport layer may have improved electron transport auxiliary ability without a substantial increase in driving voltage.

A thickness of the second electron transport layer may be about 100 Å to about 1000 Å, for example about 150 Å to about 500 Å. When the thickness of the electron transport layer is within these ranges, the electron transport layer may have satisfactory electron transporting ability without a substantial increase in driving voltage.

According to another aspect of the invention, the organic electroluminescent device further comprises an electron injection layer between the second electron transport layer and the cathode.

The electron injection layer (EIL) 36 may facilitate injection of electrons from the anode 110.

According to another aspect of the invention, the electron injection layer 36 comprises:
(i) an electropositive metal selected from alkali metals, alkaline earth metals and rare earth metals in substantially elemental form, preferably selected from Li, Na, K, Rb, Cs, Mg, Ca, Sr, Ba, Eu and Yb, more preferably from Li, Na, Mg, Ca, Sr and Yb, even more preferably from Li and Yb, most preferably Yb; and/or
(ii) an alkali metal complex and/or alkali metal salt, preferably the Li complex and/or salt, more preferably a Li quinolinolate, even more preferably a lithium 8-hydroxyquinolinolate, most preferably the alkali metal salt and/or complex of the second electron transport layer is idencial with the alkali metal salt and/or complex of the injection layer.

The electron injection layer may include at least one selected from LiF, NaCl, CsF, Li$_2$O, and BaO.

Preferably, the alkali metal salt or alkali metal organic complex in the second electron transport layer and the electron injection layer is selected the same.

A thickness of the EIL may be from about 1 Å to about 100 Å, or about 3 Å to about 90 Å. When the thickness of the electron injection layer is within these ranges, the electron injection layer may have satisfactory electron injection ability without a substantial increase in driving voltage.

A material for the anode 150 may be a metal, an alloy, or an electrically conductive compound that have a low work function, or a combination thereof. Specific examples of the material for the anode 150 may be lithium (Li), magnesium (Mg), aluminum (Al), aluminum-lithium (Al—Li), calcium (Ca), magnesium-indium (Mg—In), magnesium-silver (Mg—Ag), etc. In order to manufacture a top-emission light-emitting device, the anode 150 may be formed as a transmissive electrode from, for example, indium tin oxide (ITO) or indium zinc oxide (IZO).

According to another aspect of the invention, a method of fabricating an organic electroluminescent device (400) is provided, wherein
on an anode a hole injection layer (37), hole transport layer (31), optional a hole transport auxiliary layer (33), an emission layer (130), first electron transport layer (135), second electron transport layer (34), electron injection layer (36), and a cathode (110), are deposited in that order; or
the layers are deposited the other way around, starting with the cathode (110).

Hereinafter, the embodiments are illustrated in more detail with reference to examples. However, the present disclosure is not limited to the following examples.

DETAILED DESCRIPTION

Synthesis and physical properties of compound of formula I

Compounds of formula I may be synthesized in accordance with the methods described in PCT-KR2015-012551.

Physical properties of compounds of formula I are summarized in Table 2.

Synthesis and physical properties of compound of formula II

Compounds of formula II may be synthesized in accordance with the methods described in WO2011154131A1.

Physical properties of compounds of formula II are summarized in Table 3.

General Procedure for Fabrication of OLEDs

For top emission devices, Examples 1 to 15 and comparative examples 1 in Table 4, a glass substrate was cut to a size of 50 mm×50 mm×0.7 mm, ultrasonically cleaned with isopropyl alcohol for 5 minutes and then with pure water for 5 minutes, and cleaned again with UV ozone for 30 minutes, to prepare a first electrode. 100 nm Ag were deposited as anode at a pressure of $10^{-5}$ to $10^{-7}$ mbar.

Then, 92 wt.-% Biphenyl-4-yl(9,9-diphenyl-9H-fluoren-2-yl)-[4-(9-phenyl-9H-carbazol-3-yl)phenyl]-amine (CAS 1242056-42-3) with 8 wt.-% and 8 wt.-% of 2,2',2"-(cyclopropane-1,2,3-triylidene)tris(2-(p-cyanotetrafluorophenyl) acetonitrile) was vacuum deposited on the ITO electrode, to form a HIL having a thickness of 10 nm. Then, Biphenyl-4-yl(9,9-diphenyl-9H-fluoren-2-yl)-[4-(9-phenyl-9H-carbazol-3-yl)phenyl]-amine was vacuum deposited on the HIL, to form a HTL having a thickness of 122 nm.

Then N,N-bis(4-(dibenzo[b,d]furan-4-yl)phenyl)-[1,1':4',1"-terphenyl]-4-amine (CAS 1198399-61-9) was vacuum deposited on the HTL, to form an electron blocking layer (EBL) having a thickness of 5 nm.

Then 97 wt.-% 2-(10-phenyl-9-anthracenyl)-benzo[b]naphtho[2,3-d]furan (CAS 1627916-48-6) as EML host and 3 wt.-% blue dopant were deposited on the HTL, to form a blue-emitting EML with a thickness of 20 nm. For Examples 1 to 15 and Comparative examples 1, NUBD370 (Sun Fine Chemicals) was used as fluorescent blue dopant.

Then the first electron transport layer 135, if present, is formed with a thickness of 5 nm by depositing 2,4-diphenyl-6-(4',5',6'-triphenyl-[1,1':2',1":3",1''':3''',1''''-quinquephenyl]-3''''-yl)-1,3,5-triazine on the emission layer according to Example 1 to 15 (Table 4).

Then, the electron transport layer 34 is formed either directly on the emission layer according to comparative example 1 (Table 4), or on the first electron transport layer according to Examples 1 to 15. If the electron transport layer is in direct contact with the emission layer, the thickness is 36 nm. If the electron transport layer is deposited on top of the first electron transport layer, the thickness is 31 nm.

The electron transport layer comprises 50 wt.-% matrix compound and 50 wt.-% of LiQ.

The composition is shown in Table 4.

Then the electron injection layer 36 is formed on the electron transport layer 34 by deposing LiQ with a thickness of 1.5 nm or Yb with a thickness of 2 nm, see Tables 4.

The cathode was evaporated at ultra-high vacuum of $10^{-7}$ mbar. Therefore, a thermal single co-evaporation of one or several metals was performed with a rate of 0, 1 to 10 nm/s (0.01 to 1 Å/s) in order to generate a homogeneous cathode with a thickness of 5 to 1000 nm. The cathode was formed from 13 nm magnesium silver alloy (90:10 vol.-%) or from 11 nm Ag, see Tables 4.

A cap layer of Biphenyl-4-yl(9,9-diphenyl-9H-fluoren-2-yl)-[4-(9-phenyl-9H-carbazol-3-yl)phenyl]-amine was formed on the cathode with a thickness of 60 nm in case of MgAg cathode and 75 nm in case of Ag cathode.

The OLED stack is protected from ambient conditions by encapsulation of the device with a glass slide. Thereby, a cavity is formed, which includes a getter material for further protection.

To assess the performance of the inventive examples compared to the prior art, the current efficiency is measured under ambient conditions (20° C.). Current voltage measurements are performed using a Keithley 2400 sourcemeter, and recorded in V. At 10 mA/cm² for top emission devices, a calibrated spectrometer CAS140 from Instrument Systems is used for measurement of CIE coordinates and brightness in Candela. Lifetime LT of the device is measured at ambient conditions (20° C.) and 10 mA/cm², using a Keithley 2400 sourcemeter, and recorded in hours. The brightness of the device is measured using a calibrated photo diode. The lifetime LT is defined as the time till the brightness of the device is reduced to 97% of its initial value.

The light output in external efficiency EQE and power efficiency (1 m/W efficiency) are dertermined at 10 mA/cm² for top emission devices.

To determine the efficiency EQE in % the light output of the device is measured using a calibrated photodiode.

To determine the power efficiency in 1 m/W, in a first step the luminance in candela per square meter (cd/m2) is measured with an array spectrometer CAS140 CT from Instrument Systems which has been calibrated by Deutsche Akkreditierungsstelle (DAkkS). In a second step, the luminance is then multiplied by π and divided by the voltage and current density.

In bottom emission devices, the emission is predominately Lambertian and quantified in percent external quantum efficiency (EQE) and power efficiency in 1 m/W.

In top emission devices, the emission is forward directed, non-Lambertian and also highly dependent on the microcavity. Therefore, the external quantum efficiency (EQE) and power efficiency in 1 m/W will be higher compared to bottom emission devices.

TECHNICAL EFFECT OF THE INVENTION

Top Emission Devices

Referring to Table 4, the organic light emitting diodes according to Examples 1 to 15 exhibited improved luminance efficiency and/or life-span characteristics simultaneously compared with the organic light emitting diode according to Comparative Example 1.

In comparative example 1, a first electron transport layer (ETL) comprising a first matrix compound is not present. The electron transport layer comprising a second matrix compound of formula II and alkali metal organic complex LiQ is in direct contact with the emission layer. The operating voltage is 3.51 V, the efficiency is 6.6 cd/A and the lifetime is 52 hours.

In examples 1, a first electron transport layer is arranged between the emission layer and the second electron transport layer. The first electron transport layer consists of ETM1-2.

ETM1-2 has a glass transition temperature of 139° C., a reduction potential of −2.18 V, and a dipole moment of 0.3 Debye. The second electron transport layer has the same composition as in the comparative example. The operating voltage is reduced to 3.27 V, the efficiency is improved significantly to 7.8 cd/A and the lifetime is 40 hours.

In example 2 to 9, various compounds of formula II have been tested. The cd/A efficiency is significantly improved compared to comparative example 1.

In example 10 to 14, various compounds of formula II have been tested with a different electron injection layer and cathode. Yb has been used instead of LiQ and Ag instead of Mg:Ag alloy. The cd/A efficiency is significantly improved compared to comparative example 1.

In example 15, a compound of formula II with A=formula (IIIb) has been tested. The cd/A efficiency is significantly improved compared to comparative example 1.

In summary, much improved cd/A efficiency is obtained when a compound of formula II is used in the electron transport layer.

TABLE 2

Compounds of formula I

| Referred to as: | Compound of formula I | Tg [°C.] | Reduction potential against Fc/Fc⁺ [V] | Dipole moment [Debye] |
|---|---|---|---|---|
| ETM1-1 | | 140 | −2.22 | 0.66 |

TABLE 2-continued

Compounds of formula I

| Referred to as: | Compound of formula I | Tg [°C.] | Reduction potential against Fc/Fc+[V] | Dipole moment [Debye] |
|---|---|---|---|---|
| ETM1-2 | | 139 | −2.18 | 0.3 |
| ETM1-3 | | — | −2.23 | 1.88 |
| ETM1-4 | | 135 | −2.20 | 0.65 |

TABLE 2-continued
Compounds of formula I
| Referred to as: | Compound of formula I | Tg [°C.] | Reduction potential against Fc/Fc+[V] | Dipole moment [Debye] |
|---|---|---|---|---|
| ETM1-5 | 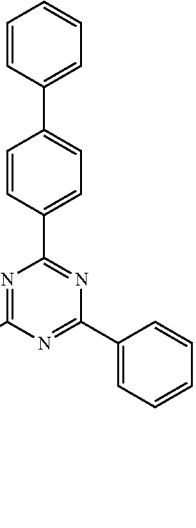 | 147 | −2.15 | — |
| ETM1-6 | 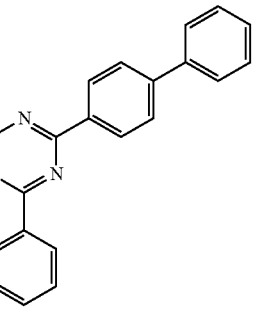 | 149 | −2.14 | — |
| ETM1-7 | 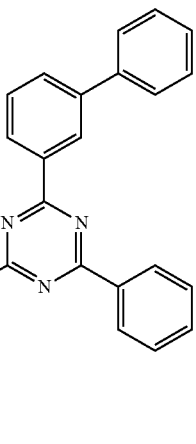 | — | −2.18 | — |

TABLE 2-continued

Compounds of formula I

| Referred to as: | Compound of formula I | Tg [°C.] | Reduction potential against Fc/Fc⁺ [V] | Dipole moment [Debye] |
|---|---|---|---|---|
| ETM1-8 | | 147 | −2.18 | 0.68 |
| ETM1-9 | | 138 | −2.20 | 0.55 |

TABLE 3

Compounds of formula II

| Referred to as: | Compound of formula II | Tg [°C.] | Reduction potential against Fc/Fc⁺ [V] | Dipole moment [Debye] |
|---|---|---|---|---|
| ETM2-1 | | 128° C. | −2.26 | 1.98 |

TABLE 3-continued
Compounds of formula II
| Referred to as: | Compound of formula II | Tg [°C.] | Reduction potential against Fc/Fc+ [V] | Dipole moment [Debye] |
|---|---|---|---|---|
| ETM2-2 | 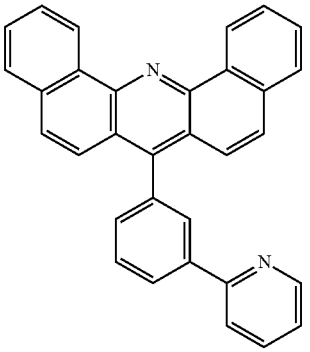 [SMILES: c1ccc(-c2cccc(-c3c4ccc5ccccc5c4nc4c3ccc3ccccc34)c2)nc1] | 92° C. | −2.29 | — |
| ETM2-3 | 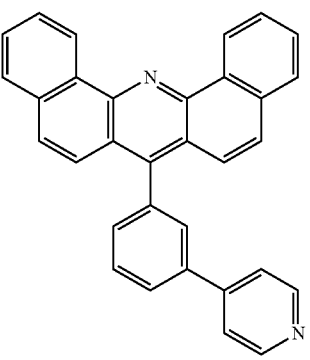 [SMILES: c1cc(-c2ccncc2)cc(-c2c3ccc4ccccc4c3nc3c2ccc2ccccc23)c1] | 98° C. | −2.27 | — |
| ETM2-4 | 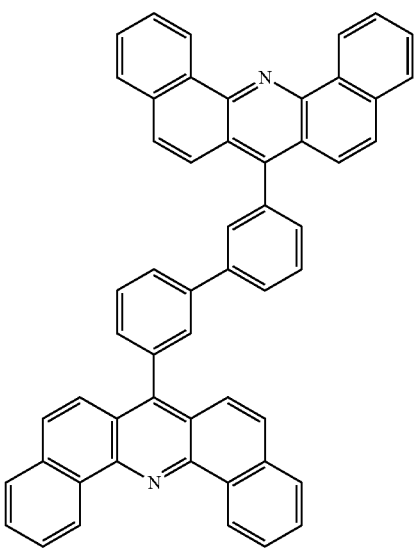 [SMILES: c1cc(-c2cccc(-c3c4ccc5ccccc5c4nc4c3ccc3ccccc34)c2)cc(-c2c3ccc4ccccc4c3nc3c2ccc2ccccc23)c1] | 181° C. | −2.25 | 2.02 |

TABLE 3-continued

Compounds of formula II

| Referred to as: | Compound of formula II | Tg [°C.] | Reduction potential against Fc/Fc+ [V] | Dipole moment [Debye] |
|---|---|---|---|---|
| ETM2-5 | | 142° C. | −2.17 | 2.17 |
| ETM2-6 | | 123° C. | −2.26 | 1.97 |
| ETM2-7 | | 121° C. | −2.26 | 2.01 |

TABLE 3-continued
Compounds of formula II
| Referred to as: | Compound of formula II | Tg [°C.] | Reduction potential against Fc/Fc+ [V] | Dipole moment [Debye] |
|---|---|---|---|---|
| ETM2-8 | 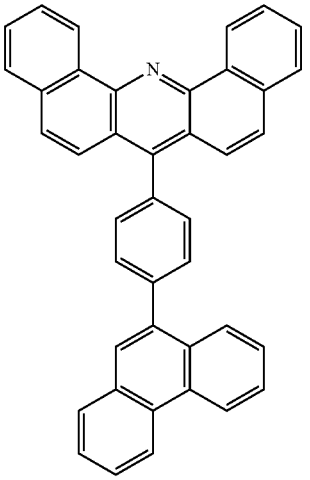 [SMILES: c1ccc2c(c1)cc(-c1ccc(-c3c4ccc5ccccc5c4nc4c3ccc3ccccc34)cc1)c1ccccc12] | 130° C. | −2.26 | 1.99 |
| ETM2-9 | 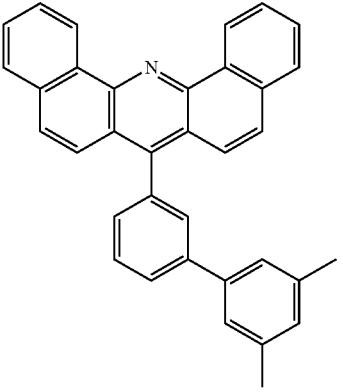 [SMILES: Cc1cc(C)cc(-c2cccc(-c3c4ccc5ccccc5c4nc4c3ccc3ccccc34)c2)c1] | 90° C. | — | — |
| ETM2-10 | 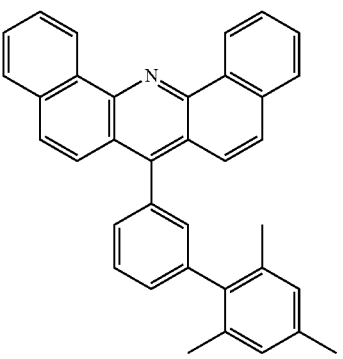 [SMILES: Cc1cc(C)c(-c2cccc(-c3c4ccc5ccccc5c4nc4c3ccc3ccccc34)c2)c(C)c1] | 85° C. | — | — |

TABLE 3-continued

Compounds of formula II

| Referred to as: | Compound of formula II | Tg [°C.] | Reduction potential against Fc/Fc⁺ [V] | Dipole moment [Debye] |
|---|---|---|---|---|
| ETM2-11 | | 116° C. | −2.28 | — |
| ETM2-12 | | 104° C. | −2.27 | — |
| ETM2-13 | | 113° C. | −2.27 | — |

TABLE 3-continued

Compounds of formula II

| Referred to as: | Compound of formula II | Tg [°C.] | Reduction potential against Fc/Fc+ [V] | Dipole moment [Debye] |
| --- | --- | --- | --- | --- |
| ETM2-14 | | Not obs. | −2.25 | — |
| ETM2-15 | | | −2.27 | 1.96 |
| ETM2-16 | | 134° C. | −2.26 | 2.04 |

TABLE 3-continued
Compounds of formula II
| Referred to as: | Compound of formula II | Tg [°C.] | Reduction potential against Fc/Fc+ [V] | Dipole moment [Debye] |
|---|---|---|---|---|
| ETM2-17 | 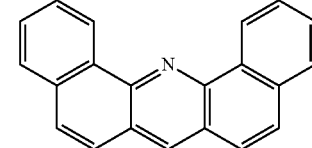 | 167° C. | −2.30 | — |
| ETM2-18 | 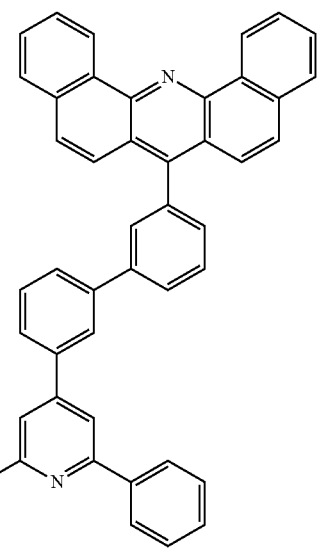 | 132° C. | −2.26 | — |
| ETM2-19 | 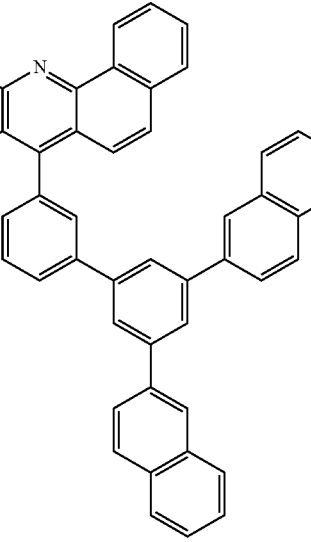 | 136° C. | −2.27 | — |

TABLE 3-continued
| | Compounds of formula II | | | |
|---|---|---|---|---|
| Referred to as: | Compound of formula II | Tg [°C.] | Reduction potential against Fc/Fc+ [V] | Dipole moment [Debye] |
| ETM2-20 | 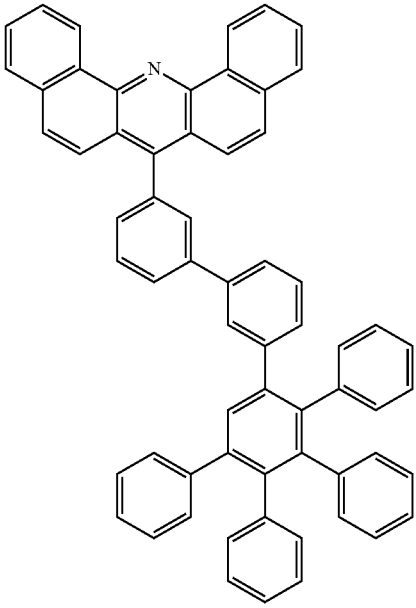 [SMILES: c1ccc(-c2cc(-c3cccc(-c4cccc(-c5c6ccc7ccccc7c6nc6c5ccc5ccccc56)c4)c3)c(-c3ccccc3)c(-c3ccccc3)c2-c2ccccc2)cc1] | 165° C. | −2.29 | 2.74 |
| ETM2-21 | 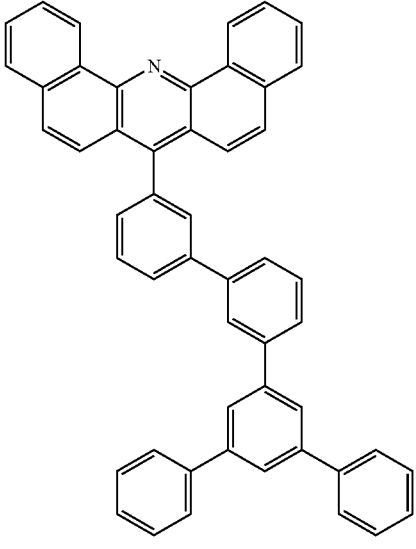 [SMILES: c1ccc(-c2cc(-c3ccccc3)cc(-c3cccc(-c4cccc(-c5c6ccc7ccccc7c6nc6c5ccc5ccccc56)c4)c3)c2)cc1] | 127° C. | −2.26 | — |

TABLE 3-continued
| | Compounds of formula II | | | |
|---|---|---|---|---|
| Referred to as: | Compound of formula II | Tg [°C.] | Reduction potential against Fc/Fc⁺ [V] | Dipole moment [Debye] |
| ETM2-22 | 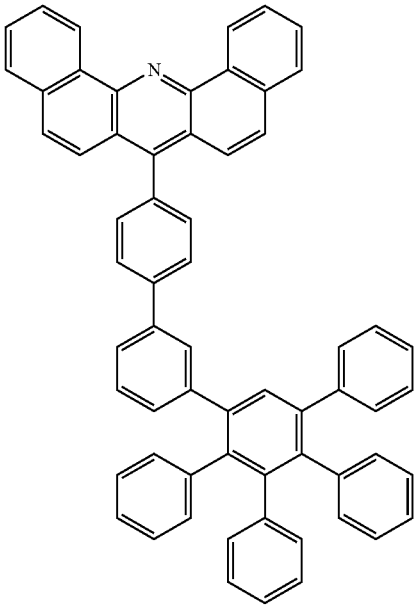 [SMILES: c1ccc(-c2cc(-c3cccc(-c4ccc(-c5c6ccc7ccccc7c6nc6c5ccc5ccccc56)cc4)c3)c(-c3ccccc3)c(-c3ccccc3)c2-c2ccccc2)cc1] | 175° C. | −2.25 | — |
| ETM2-23 | 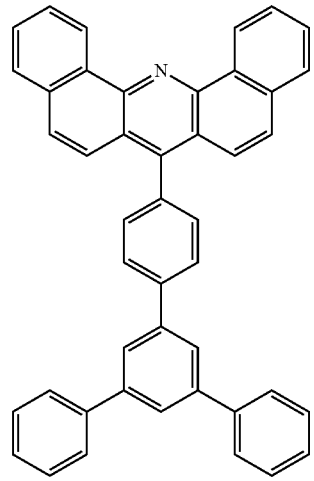 [SMILES: c1ccc(-c2cc(-c3ccccc3)cc(-c3ccc(-c4c5ccc6ccccc6c5nc5c4ccc4ccccc45)cc3)c2)cc1] | 130° C. | −2.25 | — |

TABLE 3-continued

Compounds of formula II

| Referred to as: | Compound of formula II | Tg [°C.] | Reduction potential against Fc/Fc⁺ [V] | Dipole moment [Debye] |
|---|---|---|---|---|
| ETM2-24 | | — | −2.31 | — |
| ETM2-25 | | 162° C. | — | — |

TABLE 3-continued

Compounds of formula II

| Referred to as: | Compound of formula II | Tg [°C.] | Reduction potential against Fc/Fc⁺ [V] | Dipole moment [Debye] |
|---|---|---|---|---|
| ETM2-26 | | 159° C. | −2.29 | 1.92 |
| ETM2-27 | | 148° C. | — | — |
| ETM2-28 | | 130° C. | −2.31 | — |

TABLE 3-continued
| | Compounds of formula II | | | |
|---|---|---|---|---|
| Referred to as: | Compound of formula II | Tg [°C.] | Reduction potential against Fc/Fc$^+$ [V] | Dipole moment [Debye] |
| ETM2-29 | 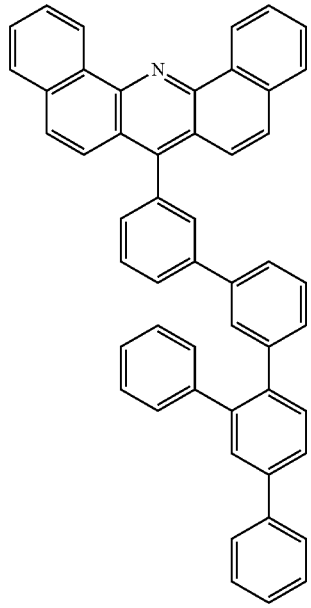 [SMILES: c1ccc(-c2ccc(-c3cccc(-c4cccc(-c5c6ccc7ccccc7c6nc6c5ccc5ccccc56)c4)c3)c(-c3ccccc3)c2)cc1] | 125° C. | −2.28 | 1.96 |
| ETM2-30 | 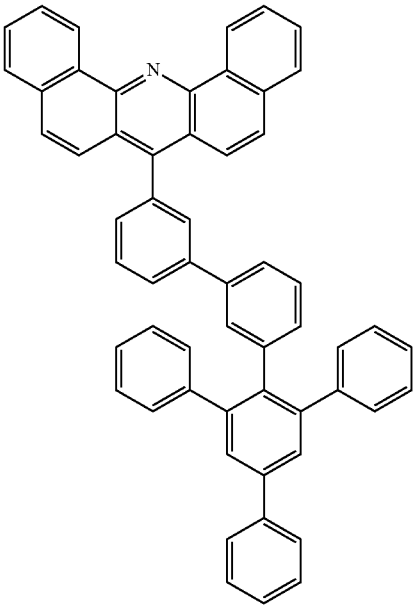 [SMILES: c1ccc(-c2cc(-c3ccccc3)c(-c3cccc(-c4cccc(-c5c6ccc7ccccc7c6nc6c5ccc5ccccc56)c4)c3)c(-c3ccccc3)c2)cc1] | 151° C. | −2.28 | 1.88 |

TABLE 3-continued

Compounds of formula II

| Referred to as: | Compound of formula II | Tg [°C.] | Reduction potential against Fc/Fc+ [V] | Dipole moment [Debye] |
|---|---|---|---|---|
| ETM2-31 | | 175° C. | — | — |
| ETM2-32 | | 130° C. | — | — |

TABLE 4

Performance at 10 mA/cm² of top emission devices comprising a first ETL (135), a second ETL (34) and a lithium organic complex, and an EIL (36)

| | First ETL | Second ETL | EIL | Cathode | Voltage (V) | Efficiency (cd/A) | LT97 (h) |
|---|---|---|---|---|---|---|---|
| Comparative example 1 | none | ETM2-5:LiQ | LiQ | Mg:Ag | 3.51 | 6.6 | 52 |
| Example 1 | ETM1-2 | ETM2-5:LiQ | LiQ | Mg:Ag | 3.27 | 7.8 | 40 |
| Example 2 | ETM1-2 | ETM2-6:LiQ | LiQ | Mg:Ag | 3.54 | 7.9 | 43 |
| Example 3 | ETM1-2 | ETM2-6:LiQ | LiQ | Mg:Ag | 3.55 | 8.1 | 50 |
| Example 4 | ETM1-2 | ETM2-6:LiQ | LiQ | Mg:Ag | 3.51 | 7.6 | 42 |
| Example 5 | ETM1-2 | ETM2-7:LiQ | LiQ | Mg:Ag | 3.43 | 8.1 | 40 |
| Example 6 | ETM1-2 | ETM2-8:LiQ | LiQ | Mg:Ag | 3.39 | 8.1 | 44 |
| Example 7 | ETM1-2 | ETM2-15:LiQ | LiQ | Mg:Ag | 3.66 | 8.7 | 39 |
| Example 8 | ETM1-2 | ETM2-16:LiQ | LiQ | Mg:Ag | 3.44 | 8.1 | 44 |
| Example 9 | ETM1-2 | ETM2-17:LiQ | LiQ | Mg:Ag | 3.57 | 8.2 | 45 |
| Example 10 | ETM1-2 | ETM2-19:LiQ | Yb | Ag | 3.56 | 8.7 | 19 |
| Example 11 | ETM1-2 | ETM2-21:LiQ | Yb | Ag | 3.54 | 8.9 | 45.5 |

TABLE 4-continued

Performance at 10 mA/cm² of top emission devices comprising a first ETL (135), a second ETL (34) and a lithium organic complex, and an EIL (36)

|  | First ETL | Second ETL | EIL | Cathode | Voltage (V) | Efficiency (cd/A) | LT97 (h) |
|---|---|---|---|---|---|---|---|
| Example 12 | ETM1-2 | ETM2-23:LiQ | Yb | Ag | 3.33 | 8.7 | 22 |
| Example 13 | ETM1-2 | ETM2-24:LiQ | Yb | Ag | 3.77 | 9.2 | 5 |
| Example 14 | ETM1-2 | ETM2-26:LiQ | Yb | Ag | 3.78 | 9.1 | 13.5 |
| Example 15 | ETM1-2 | ETM2-14:LiQ | LiQ | Mg:Ag | 3.82 | 8.8 | 28 |

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. An organic electroluminescent device comprising an anode, a cathode, an emission layer arranged between the cathode and the anode, a first electron transport layer and a second electron transport layer, wherein the first electron transport layer and the second electron transport layer are arranged between the emission layer and the cathode, the first electron transport layer is arranged closer to the emission layer than the second electron transport layer and the second electron transport layer is arranged closer to the cathode than the first electron transport layer; wherein a) the first electron transport layer comprises a first matrix compound of formula (I):

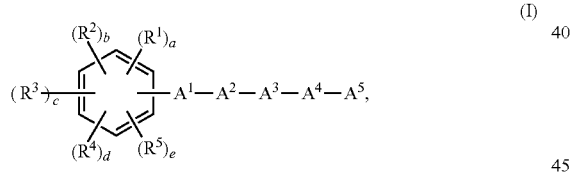

(I)

wherein $A^1$, $A^2$, $A^3$ and $A^4$ is independently selected from single bond, an unsubstituted or substituted $C_6$ to $C_{30}$ arylene and an unsubstituted or substituted $C_1$ to $C_{30}$ heteroarylene;

$A^5$ is selected from an unsubstituted or substituted $C_6$ to $C_{40}$ aryl group and/or from an unsubstituted or substituted $C_2$ to $C_{40}$ heteroaryl group, $R^1$ to $R^5$ are independently a substituted or unsubstituted $C_6$ to $C_{30}$ aryl group, a substituted or unsubstituted $C_2$ to $C_{30}$ heteroaryl group;

wherein in the substituted group, at least one hydrogen is replaced by (i) deuterium, (ii) a halogen, (iii) a $C_2$ to $C_{60}$ tertiary amino group, wherein the nitrogen atom of the tertiary amino group is substituted with two independently selected $C_1$ to $C_{30}$ hydrocarbyl groups or the nitrogen atom of the $C_2$ to $C_{60}$ tertiary amino group forms a $C_1$ to $C_{30}$ heterocyclic group, (iv) a $C_1$ to $C_{22}$ silyl group, (v) a $C_1$ to $C_{30}$ alkyl group, (vi) a $C_1$ to $C_{10}$ alkylsilyl group, (vii) a $C_6$ to $C_{22}$ arylsilyl group, (viii) a $C_3$ to $C_{30}$ cycloalkyl group, (ix) a $C_2$ to $C_{30}$ heterocycloalkyl group, (x) a $C_6$ to $C_{30}$ aryl group, (xi) a $C_2$ to $C_{30}$ heteroaryl group, (xii) a $C_1$ to $C_{20}$ alkoxy group, (xiii) a $C_1$ to $C_{30}$ perfluoro-hydrocarbyl group, (xiv) a $C_1$ to $C_{10}$ trifluoroalkyl group, or (xv) a cyano group;

a to e are independently an integer of 0 or 1 and $4 \leq a+b+c+d+e \leq 5$; and b) the second electron transport layer comprises an alkali metal salt or an alkali metal organic complex and a second matrix compound according to formula (II):

$A-W_f$(II), wherein

A is an acridine derivative of an unsubstituted or substituted benzoacridine or an unsubstituted or substituted dibenzoacridine; and W is independently selected from a substituted or unsubstituted $C_{16}$ to $C_{48}$ aryl group comprising 2 to 8 aromatic rings, or a substituted or unsubstituted $C_{10}$ to $C_{33}$ heteroaryl group comprising at least 2 to 8 aromatic rings; and the substituents of W are selected from deuterium, $C_1$ to $C_{12}$ alkyl and $C_1$ to $C_{12}$ alkoxy;

f is 1 or 2; and wherein the organic electroluminescent device further comprises an electron injection layer between the second electron transport layer and the cathode.

2. The organic electroluminescent device according to claim 1, wherein the first electron transport layer comprises a first electron matrix compound according to formula (Ia)

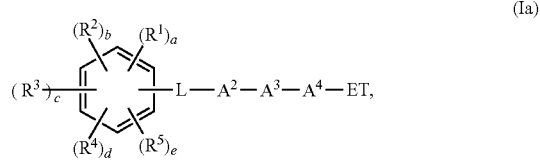

(Ia)

wherein, in formula Ia, $A^2$ is selected from $C_6$ to $C_{12}$ aryl and $C_1$ to $C_{11}$ heteroaryl;

$A^3$ and $A^4$ are a single bond; and $R^1$ to $R^5$ are independently a substituted or unsubstituted $C_6$ to $C_{30}$ aryl group, a substituted or unsubstituted $C_2$ to $C_{30}$ heteroaryl group;

a to e are independently an integer of 0 or 1 and $4 \leq a+b+c+d+e \leq 5$;

L is a single bond, a substituted or unsubstituted $C_6$ to $C_{30}$ arylene group, or a substituted or unsubstituted $C_2$ to $C_{30}$ heteroarylene group;

ET is a unsubstituted $C_6$ to $C_{40}$ aryl or a unsubstituted $C_5$ to $C_{40}$ heteroaryl group or a substituted $C_6$ to $C_{40}$ aryl or a substituted $C_5$ to $C_{40}$ heteroaryl group; and wherein in the substituted group,
at least one hydrogen is replaced by
(i) deuterium,
(ii) a halogen,
(iii) a $C_2$ to $C_{60}$ tertiary amino group, wherein the nitrogen atom of the $C_2$ to $C_{60}$ tertiary amino group is substituted with two independently selected $C_1$ to $C_{30}$ hydrocarbyl groups or forms a $C_1$ to $C_{30}$ heterocyclic group,
(iv) a $C_1$ to $C_{22}$ silyl group,
(v) a $C_1$ to $C_{30}$ alkyl group,
(vi) a $C_1$ to $C_{10}$ alkylsilyl group,
(vii) a $C_6$ to $C_{22}$ arylsilyl group,
(viii) a $C_3$ to $C_{30}$ cycloalkyl group,
(ix) a $C_2$ to $C_{30}$ heterocycloalkyl group,
(x) a $C_6$ to $C_{30}$ aryl group,
(xi) a $C_2$ to $C_{30}$ heteroaryl group,
(xii) a $C_1$ to $C_{20}$ alkoxy group,
(xiii) a $C_1$ to $C_{30}$ perfluoro-hydrocarbyl group,
(xiv) a $C_1$ to Cio trifluoroalkyl group, or
(xv) a cyano group.

3. The organic electroluminescent device according to claim 2, wherein in formula (Ia)
$R^1$ to $R^5$ are independently a substituted or unsubstituted $C_6$ to $C_{12}$ aryl group, a substituted or unsubstituted $C_5$ to $C_9$ heteroaryl group;
a to e are independently an integer of 0 or 1 and $4 \leq a+b+c+d+e \leq 5$;
L is a single bond, a substituted or unsubstituted $C_6$ to $C_{12}$ arylene group, or a substituted or unsubstituted $C_5$ to $C_9$ heteroarylene group;
ET is a unsubstituted $C_6$ to $C_{18}$ aryl or a unsubstituted $C_5$ to $C_{20}$ heteroaryl group or a substituted $C_6$ to $C_{18}$ aryl or a substituted $C_5$ to $C_{20}$ heteroaryl group; and
wherein in the substituted group, at least one hydrogen is replaced by
(xvi) deuterium,
(xvii) a $C_1$ to $C_{12}$ alkyl group,
(xviii) a $C_6$ to $C_{12}$ aryl group,
(xix) a $C_5$ to $C_9$ heteroaryl group,
(xx) a $C_1$ to $C_{12}$ alkoxy group.

4. The organic electroluminescent device according to claim 2, wherein in formula (Ia) the ET group is a $C_2$ to $C_{30}$ heteroaryl group.

5. The organic electroluminescent device according to claim 2, wherein in formula (Ia) the ET group is selected from formula E1 or E2:

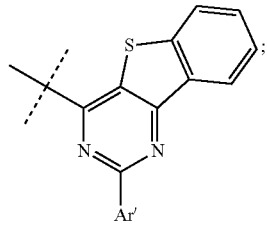

or

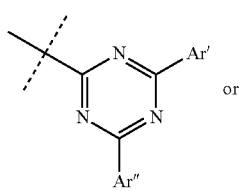

E2 wherein Ar' and Ar'' are independently selected from $C_6$ to $C_{18}$ aryl.

6. The organic electroluminescent device according to claim 5, wherein in formula (II):

A-W$_f$ (II);

A is selected from the group of formula (Ma) or (IIIb):

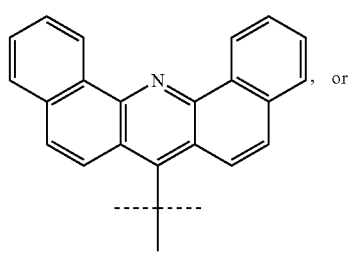

, or

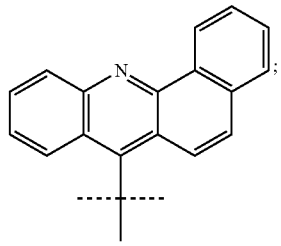

and
W is independently selected from a substituted or unsubstituted $C_{16}$ to $C_{48}$ aryl group comprising 2 to 8 aromatic rings, or a substituted or unsubstituted $C_{10}$ to $C_{33}$ heteroaryl group comprising at least 2 to 8 aromatic rings; and the substituents are
selected from deuterium, $C_1$ to $C_{12}$ alkyl and $C_1$ to $C_{12}$ alkoxy; f is 1.

7. The organic electroluminescent device according to claim 1, wherein
the alkali metal salt is selected from the group comprising LiF, LiCl, LiBr or LiI;
the alkali metal organic complex is selected from the group comprising a lithium quinolinolate, lithium borate, lithium phenolate, lithium pyridinolate or comprises a lithium with a Schiff base ligand.

8. The organic electroluminescent device according to claim 1, wherein the dipole moment of the first and/or the second electron transport matrix compound is $\geq 0$ and $\leq 2.3$ Debye.

9. The organic electroluminescent device according to claim 1, wherein the reduction potential of the first electron transport matrix compound, if measured under the same conditions by cyclic voltammetry against Fc/Fc$^+$ in tetrahydrofuran, has a value which is less negative than the value obtained for triphenylphosphine oxide and more negative than the value obtained for tetrakis(quinoxalin-5-yloxy) zirconium.

10. The organic electroluminescent device according to claim 1, wherein the emission layer comprises an emitter host and the dipole moment of the emitter host can be selected ≥0.2 Debye and ≤1.45 Debye.

11. The organic electroluminescent device according to claim 1, wherein the emission layer comprises an emitter host, and the emitter host respectively has a redox potential which, if measured under the same conditions by cyclic voltammetry against $Fc/Fc^+$ in tetrahydrofuran, has a value more negative than the respective value obtained for 7-([1,1'-biphenyl]-4-yl)dibenzo[c,h]acridine.

12. The organic electroluminescent device of claim 1, wherein the first electron transport layer is contacting sandwiched between the emission layer and the second electron transport layer, and the second electron transport layer is contacting sandwiched between the first electron transport layer and the electron injection layer.

13. A method of manufacturing an organic electroluminescent device according to claim 1, wherein
  on an anode an hole injection layer, hole transport layer, optional an electron blocking layer, an emission layer, first electron transport layer, second electron transport layer, electron injection layer, and a cathode, are deposited in that order; or
  the layers are deposited the other way around, starting with the cathode.

14. Electronic device comprising at least one organic light emitting diode, according to claim 1, the electronic device comprising at least one organic light emitting diode.

* * * * *